United States Patent
Mitas et al.

(10) Patent No.: US 7,824,857 B2
(45) Date of Patent: Nov. 2, 2010

(54) METHODS AND COMPOSITIONS FOR DIAGNOSING EPITHELIAL CELL CANCER

(75) Inventors: Michael Mitas, Mt. Pleasant, SC (US); David J. Cole, Mt. Pleasant, SC (US); William E. Gillanders, Charleston, SC (US); Michael Wallace, Ponte Vedra Beach, FL (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 11/003,223

(22) Filed: Dec. 2, 2004

(65) Prior Publication Data

US 2005/0123976 A1    Jun. 9, 2005

Related U.S. Application Data

(60) Provisional application No. 60/526,759, filed on Dec. 2, 2003.

(51) Int. Cl.
C12Q 1/68    (2006.01)
(52) U.S. Cl. ............................. 435/6; 35/7.23
(58) Field of Classification Search ............ 435/6, 435/7.1
See application file for complete search history.

(56) References Cited

U.S. PATENT DOCUMENTS

| | | | |
|---|---|---|---|
| 5,314,809 A | 5/1994 | Erlich et al. | |
| 5,814,491 A | 9/1998 | Vijg et al. | |
| 5,837,442 A | 11/1998 | Tsang | |
| 5,843,761 A | 12/1998 | Barnett et al. | |
| 5,854,003 A | 12/1998 | Lizardi | |
| 5,882,856 A | 3/1999 | Shuber | |
| 5,958,349 A | 9/1999 | Petersen et al. | |
| 6,037,129 A | 3/2000 | Cole et al. | 435/6 |
| 6,040,138 A | 3/2000 | Lockhart et al. | |
| 6,057,105 A | 5/2000 | Hoon et al. | |
| 6,183,960 B1 | 2/2001 | Lizardi | |
| 6,210,884 B1 | 4/2001 | Lizardi | |
| 6,245,517 B1 | 6/2001 | Chen et al. | |
| 6,251,601 B1 | 6/2001 | Bao et al. | |
| 6,261,776 B1 | 7/2001 | Pirrung et al. | |
| 6,306,643 B1 | 10/2001 | Gentalen et al. | |
| 6,309,823 B1 | 10/2001 | Cronin et al. | |
| 6,344,329 B1 | 2/2002 | Lizardi | |
| 6,346,413 B1 | 2/2002 | Fodor et al. | |
| 6,374,684 B1 | 4/2002 | Dority et al. | |
| 6,403,037 B1 | 6/2002 | Chang et al. | |
| 6,406,844 B1 | 6/2002 | Pirrung et al. | |
| 6,416,952 B1 | 7/2002 | Pirrung et al. | |
| 6,431,476 B1 | 8/2002 | Taylor et al. | |
| 6,440,725 B1 | 8/2002 | Pourahmadi et al. | |

7,101,663 B2    9/2006    Godfrey et al.

FOREIGN PATENT DOCUMENTS

| | | |
|---|---|---|
| EP | 1050587 | 11/2000 |
| WO | WO 95/11687 | 5/1995 |
| WO | WO 98/08970 | 3/1998 |
| WO | WO 99/13104 | 3/1999 |
| WO | WO 00/44774 | 8/2000 |
| WO | WO00/72970 | 12/2000 |
| WO | WO 00/73412 | 12/2000 |
| WO | WO 00/73413 | 12/2000 |
| WO | WO 01/01129 | 1/2001 |
| WO | WO 01/45845 | 6/2001 |
| WO | WO 01/57253 | 8/2001 |
| WO | WO 01/84463 | 11/2001 |
| WO | WO 02/18902 | 3/2002 |
| WO | WO 02/52030 | 7/2002 |
| WO | WO 02/070751 | 9/2002 |
| WO | WO 03/055973 | 7/2003 |
| WO | WO 03/072253 | 9/2003 |
| WO | WO 03/077055 | 9/2003 |
| WO | WO 2004/048931 | 6/2004 |

OTHER PUBLICATIONS

Tockman et al (Cancer Res., 1992, 52:2711s-2718s).*
Mitas et al (Clinical Chemistry, Feb. 2003, 49(2): 312-315).*
Lyegue et al (Journal of Pathology, 1999, 189: 28-33).*
Varki et al (Cancer Research, Feb. 1984, 44(2), 681-687).*
Knust et al (The EMBO Journal, 1987, 6(3):761-766).*

(Continued)

*Primary Examiner*—Sean E Aeder
(74) *Attorney, Agent, or Firm*—Needle & Rosenberg, P.C.

(57) ABSTRACT

Provided is a method for detecting metastases of epithelial cancers, comprising detecting in non-primary tissue overexpression of a nucleic acid of KS1/4, or detecting in non-primary tissue overexpression of a combination of nucleic acids of KS1/4 and PIP, of nucleic acids of KS1/4 and mam, of nucleic acids of PIP and mam, of nucleic acids of KS1/4, PIP and mam, or of nucleic acids of KS1/4 and lunx, the overexpression of a nucleic acid of KS1/4, or the overexpression of a combination of nucleic acids of KS1/4 and PIP, of nucleic acids of KS1/4 and mam, of nucleic acids of PIP and mam, of nucleic acids of KS1/4, PIP and mam, or of nucleic acids of KS1/4 and lunx in non-primary tissue being correlated with metastases of epithelial cancers.

9 Claims, 19 Drawing Sheets

OTHER PUBLICATIONS

Bosma et al (Clinical Cancer Research, Jun. 2002, 8: 1871-1877).*
Balzer et al (J Mol Med, 1999, 77:699-712).*
McLaughlin et al (Cancer Research, May 2001, 61(10):abstract).*
Liu et al (Zhonghua Zhong Liu Za Zhi, Jul. 2001, 23(4):abstract).*
Buck et al (1999, Biotechniques, 27(3):528-536).*
Helfrich et al (Br J Cancer, 1997, 76(1):abstract).*
Sjodin et al., "Dysregulated secretoglobin expression in human lung cancers," Lung Cancer, 2003, 41(1):49-56.
Varki et al., "Antigens associated with a human lung adenocarcinoma defined by monoclonal antibodies," Cancer Research, 1984, 44(2)681-687.
Mitas et al., "Lunx is a superior molecular marker for detection of non-small lung cell cancer in peripheral blood," Journal of Molecular Diagnostics, 2003, 5(4):237-242.
Perez et al., "Isolation and characterization of a cDNA encoding the ks1/4 epithelial carcinoma marker," The Journal of Immunology, 1989, 142:3662-3667.
ABI Prism 7700 Sequence Detection System, User Bulletin #5, "Multiplex PCR with TaqMan® VIC Probes," *Applied Biosystems*, pp. 1-20 (1998; Updated 2001).
Banér, et al., "Signal amplification of padlock probes by rolling circle replication," *Nucleic Acids Research*, 26(22): 5073-5078 (1998).
Bercovich, et al., "Quantitative Ratio of Primer Paris and Annealing Temperature Affecting PCR Products in Duplex Amplification," *Bio Techniques*, 27(4): 762-770 (1999).
Bostic, et al., "Limitations of Specific Reverse-Transcriptase Polymerase Chain Reaction Markers in the Detection of Metastases in the Lymph Nodes and Blood of Breast Cancer Patients," *J. Clin. Oncol.*, 16(8): 2632-2640 (1998).
Braun, et al. "Exponential DNA Replication by Laminar Convection," *Physical Review Letters*, 91(15): 158103-1 - 158103-4 (2003).
Brink, et al., "Nucleic Acid Sequence-Based Amplification, a New Method for Analysis of Spliced and Unspliced (EBV) . . . ," *J. Clin. Microbio.*, 36(11): 3164-3169 (1998).
Buck, et al., "Design Strategies and Performance of Custom DNA Sequencing Primers," *Bio Techniques*, 27(3): 528-536 (1999).
Canter, et al., "On-Chip Amplification of Genomic DNA with Short Tandem Repeat and Single Nucleotide Polymorphism Analysis," *Genetic Identity Conference Proceedings Eleventh International Symopsium on Human Identification*, Nanogen, Inc., San Diego, CA, 14 pages, (2000) (http://www.promega.com/geneticidproc/ussymp11proc/default.htm).
Chen, et al., "Accurate discrimination of pancreatic ductal adenocarcinoma and chronic pancreatitis using multimarker expression data and samples obtained by minimally invasive fine needle aspiration," *Int. J. Can.*, 120: 1511-1517 (2007).
Cheung, et al., "Natural variation in human gene expression assessed in lymphoblastoid cells," *Nat. Genetics*, 33: 422-425 (2003).
Christian, et al., "Detection of DNA point mutations and mRNA expression levels by rolling circle amplification in individual cells," *PNAS*, 98(25): 14238-14243 (2001).
D'Cunha, et al., "Molecular staging of lung cancer: Real-time polymerase chain reaction estimation of lymph node micrometastatic tumor cell burden in stage I non-small lung cancer Preliminary results of Cancer and Leukemia Group B Trial 9761," *J. Thor. Cardiov. Surg.*, 123(3): 484-491 (2002).
DeBaar, et al., "Single Rapid Real-Time Monitored Isothermal RNA Amplification Assay for Quantification of (HIV) Type 1 . . . ," *J. Clin. Microbiol.*, 39(4): 1378-1384 (2001).
DeBaar, et al., "One-Tube Real-Time Isothermal Amplification Assay To Identify and Distinguish (HIV) Type 1 Subtypes . . . ," *J. Clin. Microbiol.*, 39(5): 1895-1902 (2001).
Demidov, "Rolling-circle amplication in DNA diagnostics: the power of simplicity," *Expert Rev. Mol. Diagn.*, 2(6): 89-95 (2002),
Dessau, et al., "Coronaviruses in spinal fluid of patients with acute monosymptomatic optic neuritis," *Acta. Neurol. Scand.*, 100: 88-91 (1999).
Efron, et al., "An Introduction to the Bootstrap," *Chapman and Hall*, pp. 247-252 (1993).
"Genecard for protein-coding TACSTD1 GC02P047449: tumor-associated calcium signal," *GeneCards*, pp. 1-9 (2006).
"Genecard for protein-coding TACSTD1 GC02P047449: tumor-assocaited calcium signal," *GeneCards*, pp. 1-6 (2007 update).
Godfrey, et al., "Prognostic Value of Quantitative Reverse Transcription-Polymerase Chain Reaction . . . ," *Clinical Cancer Research*, 7: 4041-4048 (2001).
Greijer, et al., "Multiplex real-time NASBA for monitoring expression dynamics of human cytomegalovirus encoded IEI and pp. 67 RNA," *Journal of Clinial Virology*, 24: 57-66 (2002).
Harris, et al., "Typing of Dengue Viruses in Clinical Specimens and Mosquitoes by Single-Tube Multiplex Reverse Transcriptase PCR," *Jour. Clin. Microbiol.*, 36(9): 2634-2639 (1998).
Hirschhorn, et al., "A comprehensive review of genetic association studies," *Gen. Med.*, 4(2): 45-61 (2002).
Hoshikawa, et al., "Hypoxia induces different genes in the lungs of rats compared with mice," *Phyisiol. Genomics*, 12: 209-219 (2003).
Ioannidis, et al., "Replication validity of genetic association studies," *Nat. Genetics*, 29: 306-309 (2001).
Jiao, et al., "Clinical Significance of Micrometastasis in Lung and Esophageal Cancer: A New Paradigm in Thoracic Oncology," *Ann. Thorac. Surg.*, 74: 278-284 (2002).
Kerr, et al., "Bootstrapping cluster analysis: Assessing the reliability of conclusions from microarray experiments," *PNAS*, 98(16): 8961-8965 (2001).
Krishnan, et al., "PCR in Rayleigh-Bénard Convection Cell," *Science*, 298(5594): 793 (2002).
Kubuschok, et al., "Disseminated Tumor Cells in Lymph Nodes as a Determinant for Survival in Surgically Resected Non-Small-Cell Lung Cancer," *Jour. Clin. Oncology*, 17(1): 19-24 (1999).
Leone, et al., "Molecular beacon probes combined with amplification by NASBA enable homogeneous, real-time detection of RNA," *Nucleic Acids Research*, 26(9): 2150-2155 (1998).
Little, et al., "Molecular Diagnostics and Genetics," *Clinical Chemistry*, 45(6): 777-784 (1999).
Lockley, et al., "Colormetric detection of immobilised PCR products generated on a solid support," *Nucleic Acids Research*, 25(6): 1313-1314 (1997).
Luketich, et al., "Detection of Micrometastases in Histologically Negative Lymph Nodes in Esophageal Cancer," *Ann. Thorac. Surg.*, 66: 1715-1718 (1998).
Matsuda, et al., "Significance of Metastasis Detected by Molecular Techniques in Sentinel Nodes of Patients with Gastrointestinal Cancer," *Annals of Surgical Oncology*, 11(3): 250S-254S (2004).
Mikhitarian, et al., "Enhanced detection of RNA from paraffin-embedded tissue using a panal of truncated gene-specific primers for reverse transcription," *BioTechniques*, 36(3): 474-477 (2004).
Mikhitarian, et al., "An Innovative Microarray Strategy Identifies Informative Molecular Markers for the Detection of Micrometastatic Breast Cancer," *Clin. CancerRes.*, 11(10): 3697-3704 (2005).
Mitas, et al., "Accurate Discrimination of Barrett's Esophagus and Esophageal Adenocarcinoma Using a Quantitative Three-Tiered Algorithm and Multi-Marker Real-time Reverse Transcription-PCR," *Clin. Can. Res.*, 11: 2205-2214 (2005).
Mitas, et al., "Lunx is a Superior Molecular Marker for Detection of Non-Small Lung Cell Cancer in Peripheral Blood," *J. Mol. Diag.*, 5(4): 237-242 (2003).
Mitas, et al., "Real-Time Reverse Transcription-PCR Detects KS1/4 mRNA in Medistinal Lymph Nodes from Patients with Non-Small Cell Lung Cancer," *Clin. Chem.*, 49(2): 312-315 (2003).
Mitas, et al., "Quantitative Real-Time RT-PCR Detection Of Breast Cancer Micrometastasis Using A Multigene Marker Panel," *Int. J. Cancer*, 93: 162-171 (2001).
Miyake, et al., "Quantification of micrometastases in lymph nodes of colorectal cancer using real-time fluorescence ploymerase chain reaction," *Int. J. Oncol.*, 16(2): 289-293 (2000).
Mondesire, et al., "Solid-phase nucleic acid extraction, amplification, and detection," *IVD Technology Magazine* (2000).
Morrison, et al., "Quantification of Low-Copy Transcripts by Continuous SYBR® Green I Monitoring during Amplification," *BioTechniques*, 24(60): 954-962 (1998).
Nagaraju, et al., "FISSR-PCR: a simple and sensitive assay for highthroughput genotyping and genetic mapping," *Molecular and Cellular Probes*, 16: 67-72 (2002).

Nakanishi, et al., "Rapid Quantitative Detection of Carcinoembryonic Antigen-Expressing Free Tumor Cells in the Peritoneal Cavity of Gastric-Cancer Patients with Real-Time-PCR on the Lightcycler," *Int. J. Cancer (Pred. Oncol.)*, 89: 411-417 (2000).

Nallur, et al., "Signal amplification by rolling circle amplification on DNA microarrays," *Nucleic Acids Research*, 29(23) e118, pp. 1-9 (2001).

Nilsson, et al., "Making Ends Meet in Genetic Analysis Using Padlock Probes," *Human Mutation*, 19: 410-415 (2002).

Oehlenschläger, et al., "Detection of HIV-1 RNA by nucleic acid sequence-based amplification combined with fluorescence correlation spectroscopy," *PNAS*, 93: 12811-12816 (1996).

Oshima, et al., "Cloning, sequencing, and expression of cDNA for human β-glucuronidase," *PNAS USA*, 84: 685-689 (1987).

Osta, et al., "EpCAM is Overexpressed in Breast Cancer and is a Potential Target for Breast Cancer Gene Therapy," *Cancer Research*, 64: 5818-5824 (2004).

Raja, et al., "Increased Sensitivity of One-Tube, Quantitative RT-PCR," *BioTechniques*, 29(4): 702-706 (2000).

Raja, et al., "Rapid, quantitative reverse transcriptase-polymerase chain reaction: Application to intraoperative molecular detection of occult metastases in esophageal cancer," *J. Thor. Card. Surg.*, 123(3): 475-483 (2002).

Roberts, et al., "Interpretive disparity among pathologists in breast sentinel lymph node evaluation," *Am. J. Surg.*, 186: 324-329 (2003).

Sakaguchi, et al., "Clinical Relevance of Reverse Transcriptase-Polymerase Chain Reaction for the Detection of Axillary Lymph Node Metastases in Breast Cancer," *Annals of Surg. Oncol.*, 10(2): 117-125 (2003).

Schröder, et al., "Detection of Micrometastic Breast Cancer by Means of Real Time Quantitative RT-PCR and Immunostaining in Perioperative Blood Samples and Sentinel Nodes," *Int. J. Cancer*, 106: 611-618 (2003).

Schweitzer, et al., "Combining nucleic acid amplification and detection," *Curr. Opin. Biotechnol.*, 12: 21-27 (2001).

Schweitzer, et al., "Immunoassays with rolling circle DNA amplification: A versatile platform for ultrasensitive antigen detection," *PNAS*, 97(18): 10113-10119 (2000).

Silva, et al., "Detection of epithelial tumour RNA in the plasma of colon cancer patients is associated with advanced stages and circulating tumour cells," *Gut.*, 50: 530-534 (2002).

"TaqMan® One-Step RT-PCR Master Mix Reagents Kit: Protocol," *Biosystems*, pp. 1-26 (1999).

Thomas, et al., "Amplification of Padlock Probes for DNA Diagnostics by Cascade Rolling Circle Amplification or the Polymerase Chain Reaction," *Arch. Pathol. Lab Med.*, 123: 1170-1176 (1999).

Troutt, et al., "Ligation-anchored PCR: A simple amplification technique with single-sided specificity," *PNAS USA*, 89: 9823-9825 (1992).

Viehmann, et al., "Multiplex PCR - a rapid screening method for detection of gene rearrangements in childhood acute lymphoblastic leukemia," *Annals of Hematol.*, 78: 157-162 (1999).

Wallace, et al., "Accurate Molecular Detection of Non-small Cell Lung Cancer Metastases in Mediastinal Lymph Nodes Sampled by Endoscopic Ultrasound-Guided Fine Needle Aspiration,"*Chest*, 127(2): 430-437 (2005).

Wu, et al., "The Effect of Temperature and Oligonucleotide Primer Length on the Specificity and Efficiency of Amplification by Polymerase Chain Reaction," *DNA and Cell Biology*, 10(3): 233-238 (1991).

Ylitalo, et al., "Detection of Genital Human Papillomavirus by Single-Tube Nested PCR and Type-Specific Oligonucleotide Hybridization," *Jour. Clin. Microb.*, pp. 1822-1828 (1995).

NCBI Accession NM_000213, ITGB4, The NCBI handbook (Internet). Bethesda (MD): Natl Lib Med-(US), 2002, Ch. 18 The RefSeq Project. http://www.ncbi.nlm.nih.gov/entrez/query.fcgi?db=Books.

NCBI Accession NM_000224, CK18, The NCBI handbook [Internet]. Bethesda (MD): Natl Lib Med (US), 2002, Ch. 18 The RefSeq Project. http://www.ncbi.nlm.nih.gov/entrez/query.fcgi?db=Books.

NCBI Accession NM_000245, c-MET, The NCBI handbook [Internet]. Bethesda (MD): Natl Lib Med (US), 2002, Ch. 18 The RefSeq Project. http//www.ncbi.nlm.nih.gov/entreequery.fcgi?db=Books.

NCBI Accession NM_, TYR, The NCBI handbook [Internet]. Bethesda (MD): Natl Lib Med (US), 2002, Ch. 18 The RefSeq Project. http//www.ncbi.nlm.nih.govientrez/query.fcgi?db=Books.

NCBI Accession NM_000453,NIS, The NCBI handbook [Internet]. Bethesda (MD): Natl Lib Med (US), 2002, Ch. 18 The RefSeq Project. http//www.ncbi.ntm.nih.gov/entrez/query.fcgi?db=Books.

NCBI Accession NM_000542, SFTPB, The NCBI handbook [Internet]. Bethesda (MD): Natl Lib Med (US), 2002, Ch. 18 The RefSeq Project. http//www.ncbi.nlm.nih.gov/entreziquery.fcgi?db=Books.

NCBI Accession NM_000526, CK14, The NCBI handbook [Internet]. Bethesda (MD): Natl Lib Med (US), 2002, Ch. 18 The RefSeq Project. http//www.ncbi.nlm.nih.gov/entrez/query.fcgi?db=Books.

NCBI Accession NM_000737,BHCG, The NCBI handbook [Internet]. Bethesda (MD): Natl Lib Med (US), 2002, Ch. 18 The RefSeq Project. http//www.ncbinlm.nih.gov/entrez/query.fcgi?db=Books.

NCBI Accession NM_001169, Survivin, The NCBI handbool [Internet]. Bethesda (MD): Natl Lib Med (US), 2002, Ch. 18 The RefSeq Project. http//www.ncbi.nlm.nih.govientreziquery.fogadb=Books.

NCBI Accession NM_001168, SSXu, The NCBI handbook [Internet]. Bethesda (MD): Natl Lib Med (US), 2002, Ch. 18 The RefSeq Project. http//www.ncbi.nlm.nih.govientrez/query.fcgi?db=Books.

NCBI Accession NM_001187, BAGE, The NCBI handbook [Internet]. Bethesda (MD): Natl Lib Med (US), 2002, Ch. 18 The RefSeq Project. http//www.ncbi.nlm.nih.gov/entrez/query.fcgi?db=Books.

NCBI Accession NM_001327, CTAG1, The NCBI handbook [Internet]. Bethesda (MD): Natl Lib Med (US), 2002, Ch. 18 The RefSeq Project. http//www.ncbi.nlm.nih.gov/entrez/query.fcgi?db=Books.

NCBI Accession NM_001468, GAGE1, The NCBI handbook [Internet]. Bethesda (MD): Natl Lib Med (US), 2002, Ch. 18 The RefSeq Project. http//www.ncbi.nlm.nih.gov/entrez/query.fcgi?db=Books.

NCBI Accession NM_001726, BRDT, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_001944, PVA, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_002276, CK19 The NCBI handbook (Internet). Bethesda (MD): Natl Lib Med (US), 2002, CH. 18 The RefSeq Project. http//www.ncbi.nlm.nih.govientrez/query.fcgi?db=Books.

NCBI Accession NM_002281, KRTHBI, The NCBI handbook (Internet). Bethesda (MD): Natl Lib Med (US), 2002, CH. 18 The RefSeq Project. http//www.ncbi.nlm.nih.govientrez/query.fcgi?db=Books.

NCBI Accession NM_002354, TACSTDI, The NCBI handbook (Internet). Bethesda (MD): Natl Lib Med (US), 2002, Ch. 18 The RefSeq Project. http//www.ncbi.nlm.nih.goWentrez/query.fcgi?db=Books.

NCBI Accession NM_002362, MAGEA4, The NCBI handbook [Internet]. Bethesda (MD): Natl Lib Med (US), 2002, CH. 18 The RefSeq Project. h tp//www.ncbi.nlm.nih.govientrez/query.fcgi?db=Books.

NCBI Accession NM_002407, The NCBI handbook (Internet). Bethesda (MD): Natl Lib Med (US), 2002, CH. 18 The RefSeq Project. http//www.ncbi.nlm.nih.gov/entrez/query.fcgi?db=Books.

NCBI Accession NM_002411, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_002423, MMP7, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_002652, PIP, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_002820, PTHrP, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_002974, SCCA2, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_003219, HTERT, The NCBI handbook (Internet). Bethesda (MD): Natl Lib Med (US), 2002, CH. 18 The RefSeq Project. http//www.ncbi.nlm.nih.gov/entrez/query.fcgi?db=Books.

NCBI Accession NM_003317, TITF1, The NCBI handbook [Internet]. Bethesda (MD): Natl Lib Med (US), 2002, CH. 18 The RefSeq Project. http//www.ncbi.nlm.nih.govientrez/query.fcgi?db=Books.

NCBI Accession NM_004362, CEA, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_004616, TM4SF3. The NCBI handbook (Internet). Bethesda (MD): Natl Lib Med (US), 2002, CH. 18 The RefSeq Project. http//www.ncbi.nlm.nih.govientredquery.fcgi?db=Books.

NCBI Accession NM_004988, MAGEA1, The NCBI handbook [Internet]. Bethesda (MD): Natl Lib Med (US), 2002, CH. 18 The RefSeq Project. http//www.ncbi.nlm.nih.govientreziquery.fcgi7db=Books.

NCBI Accession NM_005361,MAGEA2, The NCBI handbook [Internet]. Bethesda (MD): Natl Lib Med (US), 2002, CH. 18 The RefSeq Project. http//www.ncbl.ntm.nih.govientreziquery.fcgi?db=Books.

NCBI Accession NM_005362, MAGEA3, The NCBI handbook [Internet]. Bethesda (MD): Natl Lib Med (US), 2002, CH. 18 The RefSeq Project. http//www.ncbi.nlm.nih.govientrez/query.fcrdb=Books.

NCBI Accession NM_005364, MAGEAB, The NCBI handbook [Internet]. Bethesda (MD): Natl Lib Med (US), 2002, CH. 18 The RefSeq Project. http//www.ncbi.nlm.nih.gov/entrez/query.fcgi7db=Books.

NCBI Accession NM_005367, MAGEAI2, The NCBI handbook (Internet). Bethesda (MD): Natl Lib Med (US), 2002, CH. 18 The RefSeq Project. http//www.ncbi.nlm.nih.gov/entrez/query.fcgi?db=Books.

NCBI Accession NM_005556, CK7, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_006011, SSX2, The NCB! handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_006183, NTS, The NCBI handbook (Internet). Bethesda (MD): Natl Lib Med (US), 2002, CH. 18 The RefSeq Project. http//www.ncbi.nlm.nih.gov/entrez/query.fcgi?db=Books.

NCBI Accession NM_006919, SCCA1, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_007127, Viilin 1, The NCBI handbook [Internet]. Bethesda (MD): Natl Lib Med (US), 2002, CH. 18 The RefSeq Project. http//www.ncbi.nlm.nih.govientreziquery.fcgi?db=Books.

NCBI Accession NM_014419, SGY-1, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

NCBI Accession NM_017448, LUNX, The NCBI handbook (Internet). Bethesda (MD): Natl Lib Med (US), 2002, CH. 18 The RefSeq Project. http//www.ncbi.nlm.nih.gov/entrez/query.fcgi?db=Books.

NCBI Accession NM_019010, CK20, The NCBI handbook (Internet). Bethesda (MD): Natl Lib Med (US), 2002, CH. 18 The RefSeq Project. http//www.ncbi.nlm.nih.govientrez/query.fcgi?db=Books.

NCBI Accession NM_021048, MAGEA10, The NCBI handbook (Internet). Bethesda (MD): Natl Lib Med (US), 2002, CH. 18 The RefSeq Project. http//www.ncbi.nlM.nih.gov/entrez/query.fcgi7db=Books.

NCBI Accession NM_130852, LDHC, The NCBI handbook [Internet]. Bethesda (MD): Natl Lib Med (US), 2002, CH. 18 The RefSeq Project. http//www.ncbi.nlm.nih.gov/entrez/query.fcgi?db=Books.

Balzar et al., "The biology of the 17-1A antigen (Ep-CAM)," *J. Mol. Med.*, 77:699-712 (1999).

Perez et al., "Isolation and characterization of a cDNA encoding the KS1/4 epithelial carcinoma marker," *J. Immunology*, 142:3662-3667 (1989).

Sjödin et al., "Dysregulated secretoglobin expression in human lung cancers," *Lung Cancer*, 2003, 41(1):49-56.

Mitas et al., "Quantitative Real-Time RT-PCR detection of Breast Cancer Micrometastasis Using a Multigene Marker Panel," Int. J Cancer, vol. 93, No. 2, pp. 162-171 (2001).

U.S. Appl. No. 12/152,423, Mitas, Michael, filed May 13, 2008, Notice of Publication, Oct. 2, 2008.

U.S. Appl. No. 12/152,423, Mitas, Michael, filed May 13, 2008, Non-Final Rejection, Sep. 26, 2008.

U.S. Appl. No. 12/152,423, Mitas, Michael, filed May 13, 2008, Preliminary Amendment, May 13, 2008.

U.S. Appl. No. 12/152,423, Mitas, filed May 13, 2008, Abandoment, Apr. 7, 2009.

U.S. Appl. No. 11/711,493, Mitas, filed Feb. 27, 2007, Non-Final Rejection, Jul. 21, 2009.

U.S. Appl. No. 11/711,493, Mitas, filed Feb. 27, 2007, Response to Election / Restriction Filed, May 11, 2009.

U.S. Appl. No. 11/711,493, Mitas, filed Feb. 27, 2007, Requirement for Restriction/Election, Mar. 10, 2009.

Abba et al., "Gene Expression Signature of Estrogen Receptor a Status in Breast Cancer," BMC Genomics, 6:37:1-13 2005.

Aronow et al., "Microarray Analysis Of Trophoblast Differentiation: Gene Expression Reprogramming in Key Gene Function Categories," Physiol. Genomics, 6:105-116, 2001.

Arumugam et al., "S100P Promotes Pancreatic Cancer Growth, Survival, and Invasion," Clin. Cancer Res., 11(15):5356-5364, 2005.

Barasch et al., "Mesenchymal to Epithelial Conversion in Rat Metanephros Is Induced by LIF," Cell, 99:377-386, 1999.

Barasch, "Genes and Proteins Involved in Mesenchymal to Epithelial Transition," Curr. Opin. Nephrol. Hypertens., 10:429-436, 2001.

Bates & Mercurio, "The Epithelial-Mesenchymal Transition (EMT) and Colorectal Cancer Progression," Cancer Biol. Ther., 4:365-370, 2005.

Berger et al., "Evaluation of Three mRNA Markers for the Detection of Lymph Node Metastases," Anticancer Res, 26:3855-3860, 2006.

Cappelletti et al., "Prognostic Relevance of pS2 Status in Association With Steroid Receptor Status and Proliferative Activity in Node-negative Breast Cancer," Eur. J. Cancer 28A, No. 8/9:1315-1318, 1992.

Cardoso et al., "Potential Predictive Value of Bcl-2 for Response to Tamoxifen in the Adjuvant Setting of Node-Positive Breast Cancer," Clin. Breast Cancer, vol. 5:364-369, 2004.

Cerfolio et al., "The Role of FDG-PET Scan in Staging Patients With Nonsmall Cell Carcinoma," Ann. Thorac. Surg. 76:861-866, 2003.

Choi et al., "Mediastinoscopy in Patients With Clinical Stage I Non-Small Cell Lung Cancer." Ann. Thorac. Surg. 75:364-366, 2003.

Corradini et al., "Maspin and Mammaglobin Genes Are Specific Markers for RT-PCR Detection of Minimal Residual Disease in Patients With Breast Cancer," Ann Oncol, 12:1693-1698, 2001.

Cote et al., "Role of Immunohistochemical Detection of Lymph-Node Metastases in Management of Breast Cancer," Lancet, vol. 354:896-900, 1999.

Coughlin et al., "Role of Mediastinoscopy in Pretreatment Staging of Patients with Primary Lung Cancer," Ann. Thorac. Surg. vol. 40, No. 6:556-560, 1985.

de Mascarel et al., "Prognostic Significance of Breast Cancer Axillary Lymph Node Micrometastases Assessed by Two Special Techniques: Reevaluation With Longer Follow-Up," Br. J. Cancer 66(3):523-527.

Endoh et al., "Prognostic Model of Pulmonary Adenocarcinoma by Expression Profiling of Eight Genes As Determined by Quantitative Real-Time Reverse Transcriptase Polymerase Chain Reaction," J. Clin. Oncol. vol. 22, No. 5:811-819, 2004.

Esworthy et al., "Epithelium-Specific Glutathione Peroxidase, Gpx2, Is Involved in the Prevention of Intestinal Inflammation in Selenium-Deficient Mice," J. Nutr., 135:740-745, 2005.

Fisher et al., "The Accuracy of Clinical Nodal Staging and of Limited Axillary Dissection as a Determinant of Histologic Nodal Status in Carcinoma of the Breast," Surg. Gynecol. Obstet. 152:765-772, 1981.

Fleming et al., "Mammaglobin, a Breast-Specific Gene, and Its Utility as a Marker for Breast Cancer," Ann N Y Acad Sci 923:78- 89 2000.

Fletcher et al., "hAG-2 and hAG-3, Human Homologues of Genes Involved in Differentiation, are Associated With Oestrogen Receptor-Positive Breast Tumours and Interact With Metastasis Gene C4.4a and Dystroglycan," Br. J. Cancer 88:579-585, 2003.

Foekens et al., "Prediction of Relapse and Survival in Breast Cancer Patients by pS2 Protein Status," Cancer Res. 50:3832-3837, 1990.

Foekens et al., "Relationship of PS2 With Response to Tamoxifen Therapy in Patients With Recurrent Breast Cancer," Br. J. Cancer 70:1217-1223, 1994.

Gardner and Feldman, "Are Positive Axillary Nodes in Breast Cancer Markers for Incurable Disease?," Ann. Surg. vol. 218, No. 3:270-278, 1993.

Ge et al., "Detection of Disseminated Lung Cancer Cells in Regional Lymph Nodes by Assay of CK19 Reverse Transcriptase Polymerase Chain Reaction and Its Clinical Significance," J Cancer Res. Clin. Oncol. 131:662-668, 2005.

Gillanders et al., "Molecular Detection of Micrometastatic Breast Cancer in Histopathlogy-Negative Axillary Lymph Nodes Correlates with Traditional Predictors of Prognosis," Ann. Surg. vol. 239, No. 6:828-840, 2004.

Gonzalez-Stawinski et al., "A Comparative Analysis of Positron Emission Tomography and Mediastinoscopy in Staging Non-Small Cell Lung Cancer." J. Thorac. Cardiovasc. Surg. 126:19001904, 2003.

Grünewald et al., "Mammaglobin Gene Expression: A Superior Marker of Breast Cancer Cells in Peripheral Blood in Comparison to Epidermal-Growth-Factor Receptor and Cytokeratin-19," Lab Invest 80(7):1071-1077, 2000.

Grätzmann, et al., "Microarray-based Gene Expression Profiling in Pancreatic Ductal Carcinoma: Status Quo and Perspectives," Int J Colorect Dis 19:401-413 (2004).

Gu et al., "Detection of Micrometastatic Tumor Cells in pN0 Lymph Nodes of Patients With Completely Resected Nonsmall Cell Lung Cancer," Ann. Surg.vol. 235, No. 1:133-139, 2002.

Gutierrez et al., " Molecular Changes in Tamoxifen-Resitant Breast Cancer: Relationship Between Estrogen Receptor, HER-2, and p38 Mitogen-Activated Protein Kinase," J. Clin. Oncol. vol. 23, No. 11:2469-2476, 2005.

Henderson, "Assessing Test Accuracy and Its Clinical Consequences: A Primer for Receiver Operating Characteristic Curve Analysis," Ann. Clin. Biochem. 30:521-539, 1993.

Henry et al., "pNR-2/pS2 immunohistochemical staining in breast cancer: correlation with prognostic factors and endocrine response," Br. J. Cancer 63:615-622, 1991.

Hogan et al., "Rap1 Regulates the Formation of E-Cadherin-Based Cell-Cell Contacts," Mol.Cell Biol. vol. 24, No. 15:6690-6700, 2004.

Huber et al., "Molecular Requirements for Epithelial-Mesenchymal Transition During Tumor Progression," Curr. Opin. Cell Biol. 17:548-558, 2005.

International (Ludwig) Breast Cancer Study Group, " Clinical Practice: Prognostic Importance of Occult Axillary Lymph Node Micrometastases From Breast Cancers," The Lancet. 335:1565-1568, 1990.

Janssens et al., "Housekeeping Genes as Internal Standards in Cancer Research," Mol. Diagn. 8:107-113, 2004.

Kobayashi et al., "A Kunitz-type Protease Inhibitor, Bikunin, Inhibits Ovarian Cancer Cell Invasion by Blocking the Calcium-dependent Transforming Growth Factor-β1 Signaling Cascade," J. Biol. Chem. vol. 278, No. 10:7790-7799, 2003.

Le Pimpec-Barthes et al., "Association of CK19 mRNA Detection Of Occult Cancer Cells in Mediastinal Lymph Nodes in Non-Small Cell Lung Carcinoma and High Risk of Early Recurrence," Eur. J Cancer 41:306-312, 2005.

Levashova et al., "Conditionally Immortalized Cell Line of Inducible Metanephric Mesenchyme," Kidney Int. 63:2075-2087, 2003.

Liu et al., "Human Homologue of Cement Gland Protein, a Novel Metastasis Inducer Associated with Breast Carcinomas," Cancer Res. 65 (9):3796-3805, 2005.

Livak and Schmittgen, "Analysis of Relative Gene Expression Data Using Real-time Quantitative PCR and the $2^{*\Delta\Delta C}{}_T$ Method," Methods 25:402-408, 2001.

Manni et al., "Estrogen and Progesterone Receptors in the Prediction of Response of Breast Cancer to Endocrine Therapy," Cancer 46:2838-2841, 1980.

Marazuela et al., "Expression of MAL2, an Integral Protein Component of the Machinery for Basolateral-to-Apical Transcytosis, in Human Epithelia," J. Histochem. Cytochem. 52:243-252, 2004.

Marchetti et al., "mRNA Markers of Breast Cancer Nodal Metastases: Comparison Between Mammaglobin and Carcinoembryonic Antigen in 248 Patients," J. Pathol 195(2):186-190, 2001.

McGuckin et al., "Occult Axillary Node Metastases in Breast Caccer: Their Detection and Prognostic Significance," Br. J. Cancer 73:88-95, 1996.

McGuire et al., "Current Status of Estrogen and Progesterone Receptors in Breast Cancer," Cancer 39:2934-2947, 1977.

Meng et al., "Human ADA3 Binds to Estrogen Receptor (ER) and Functions As a Coactivator for ER-mediated Transactivation," J. Biol. Chem. vol. 279, No. 52:54230-54240, 2004.

Min et al., "Identification of Superior Markers for Polymerase Chain Reaction Detection of Breast Cancer Metastases in Sentinel Lymph Nodes," Cancer Res. 58:4581-4584, 1998.

Mitas et al., "Prostate-Specific Ets (PSE) factor: A Novel Marker for Detection of Metastatic Breast Cancer in Axillary Lymph Nodes," British Journal of Cancer 86:899-904, 2002.

Nissan et al.,"Multimarker RT-PCR Assay for the Detection of Minimal Residual Disease in Sentinel Lymph Nodes of Breast Cancer Patients," Br J Cancer 94:681-685, 2006.

Ohta et al., "Can Tumor Size Be a Guide for Limited Surgical Intervention in Patients With Peripheral Non-Small Cell Lung Cancer? Assessment From the Point of View of Nodal Micrometastasis," J. Thorac. Cardiovasc. Surg. 122:900-906, 2001.

Okada et al., "Effect of Tumor Size on Prognosis in Patients With Non-Small Cell Lung Cancer: The Role of Segmentectomy As A Type Lesser Resection," J. Thorac. Cardiovasc. Surg. 129:8793, 2005.

Osaki et al., "Prognostic Impact of Micrometastatic Tumor Cells in the Lymph Nodes and Bone Marrow of Patients With Completely Resected Stage I Non-Small-Cell Lung Cancer," J. Clin. Oncol. 20:2930-2936, 2002.

Ouellette et al., "RT-PCR for Mammaglobin Genes, *MGB1* and *MGB2*, Identifies Breast Cancer Micrometastases in Sentinel Lymph Nodes," Am J Clin Pathol, 121(5):637-643, 2004.

Paik et al., "A Multigene Assay to Predict Recurrence of Tamoxifen-Treated, Node-Negative Breast Cancer," N. Engl. J. Med. 351:2817-2826, 2004.

Patterson et al., "A Prospective Evaluation of Magnetic Resonance Imaging, Computed Tomography, and Mediastinoscopy in the Preoperative Assessment of Mediastinal Node Status in Bronchogenic Carcinoma," J. Thorac. Cardiovasc. Surg. 94:679-684, 1987.

Patz et al., "Thoracic Nodal Staging With PET Imaging With 18FDG in Patients With Bronchogenic Carcinoma," Chest 108:1617-1621, 1995.

Petek et al., "Localization of the Human Anterior Gradient-2 Gene (AGR2) To Chromosome Band 7p21.3 By Radiation Hybrid Mapping And Fluorescence In Situ Hybridisation," Cytogenet. Cell Genet. 89:141-142, 2000.

Petz et al., "Differential Regulation Of The Human Progesterone Receptor Gene Through An Estrogen Response Element Half Site And Sp1 Sites," J. Steroid Biochem. Mol. Biol. 88:113-122, 2004.

Pohler et al., "The Barrett's Antigen Anterior Gradient-2 Silences the p53 Transcriptional Response to DNA Damage" Mol. Cell Proteomics 3:534-547, 2004.

Ribieras et al., "The pS2/TFF1 Trefoil Factor, From Basic Research to Clinical Applications," Biochim. Biophys. Acta 1378:F61-F77, 1998.

Rio et al., "Specific Expression Of The Ps2 Gene In Subclasses Of Breast Cancers In Comparison With Expression Of The Estrogen and Progesterone Receptors And The Oncogene ERBB2," Proc. Natl. Acad. Sci. USA 84:9243-9247, 1987.

Saimura et al., "Prognosis of a Series of 763 Consecutive Node-Negative Invasive Breast Cancer Patients Without Adjuvant Therapy: Analysis of Clinicopathlogical Prognostic Factor," J Surg. Oncol. 71: p. 101-105, 1999.

Schena et al., "Parallel Human Genome Analysis: Microarray-Based Expression Monitoring of 1000 Genes," Proc. Natl. Acad. Sci. USA 93:10614-10619, 1996.

Schmittgen et al., "Quantitative Reverse Transcription-Polymerse Chain Reaction to Study mRNA Decay: Comparison of Endpoint and Real-Time Methods," Anal. Biochem. 285:194-204, 2000.

Schultz et al., "Estrogen Receptor $\alpha$ and Sp1 Regulate Progesterone Receptor Gene Expression," Mol. Cell Endocrinol. 201:165-175, 2003.

Seshadri et al., "The Relative Prognostic Significance of Total Cathepsin D and Her-2/*neu* Oncogene Amplification in Breast Cancer," Int. J. Cancer 56:61-65, 1994.

Smid et al., "Genes Associated With Breast Cancer Metastatic to Bone," J Clin Oncol, 24(15):2261-2267, 2006.

Smirnov et al., "Global Gene Expression Profiling of Circulating Tumor Cells," Cancer Res. 65:4993-4997, 2005.

Specht et al., "Quantitative Gene Expression Analysis in Microdissected Archival Formalin-Fixed and Paraffin-Embedded Tumor Tissue," Am. J. Pathol. 158:419-429, 2001.

Spruance et al., "Hazard Ratio in Clinical Trials," Antimicrob. Agents & Chemo. 48(8):2787-2792, 2004.

Strauss et al., "Randomized Clinical Trial of adjuvant chemotherapy with paclitaxel and carboplatin following resection in Stage IB Non-Small Cell Lung Cancer (NSCLC): Report of Cancer and Leukemia Group B (CALGB) Protocol 9633," J. Clin. Oncol. 22, No. 14S:7019, 2004 (Abstract).

Sun et al., "Estrogen regulation of trefoil factor 1 expression by estrogen receptor $\alpha$ and Sp proteins," Exp. Cell Res. 302:96-107, 2005.

Thompson et at., "hAG-2, the Human Homologue of the *Xenopus laevis* Cement Gland Gene XAG-2, Is Coexpressed with Estrogen Receptor in Breast Cancer Cell Lines," Biochem. Biophys. Res. Commun. 251:111-116, 1998.

Watson and Fleming, "Mammaglobin, a Mammary-specific Member of the Uteroglobin Gene Family, Is Overexpressed in Human Breast Cancer," Cancer Res. 56:860-865, 1996.

Watson et al., "Mammaglobin Expression in Primary, Metastatic, and Occult Breast Cancer," Cancer Res 59(13):3028-3031, 1999.

Weigelt et al., "Detection of Metastases in Sentinel Lymph Nodes Of Breast Cancer Patients By Multiple mRNA Markers," Br J Cancer 90(8):1531-1537, 2004.

Winton et al., "Vinorelbine plus Cisplatin vs. Observation in Resected Non-Small-Cell Lung Cancer," N. Engl. J. Med. 352:2589-2597, 2005.

Wisnivesky et al., "The Effect of Tumor Size on Curability of Stage I Non-small Cell Lung Cancers," Chest 126: p. 761-765, 2004.

Wu et al., "Nodal Occult Metastasis in Patients With Peripheral Lung Adenocarcinoma of 2.0 cm or Less in Diameter," Ann. Thorac. Surg. 71:1772-1778, 2001.

Yang et al., "Twist, a Master Regulator of Morphogenesis, Plays an Essential Role in Tumor Metastasis," Cell 117:927-939, 2004.

Zach et al., "Statistical Validation of the Mammaglobin-Nested RT-PCR Assay for Tumor Cell Detection in Blood of Breast Cancer Patients," Biotechniques 31(6):1358-1362, 2001.

Zheng et al., "Variation of ER status between primary and metastatic breast cancer and relationship to p53 expression," Steroids 66:905-910, 2001.

\* cited by examiner

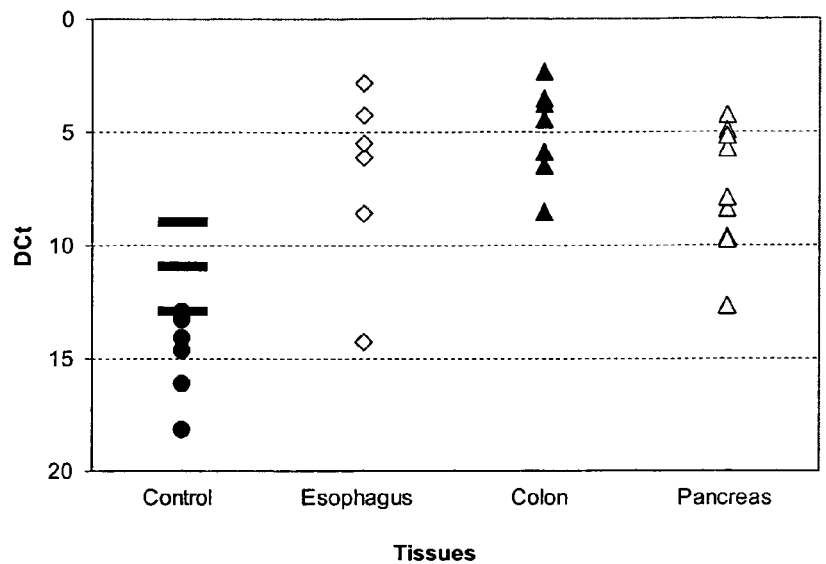

Figure 1. KS1/4 is overexpressed in lymph nodes obtained from esophageal, colon, and pancreatic cancer patients. In this experiment, samples were obtained from negative control (n=6) lymph nodes, and metastatic lymph nodes derived from esophageal (n=6), colon (n=8) and pancreatic (n=11) cancer patients. For cancer tissue, each sample was determined to have metastatic disease as determined by H&E analysis. Expression levels of KS1/4 were measured in lymph node tissues by real-time RT-PCR compared to a reference control gene. Expression levels are measured in DCt values, which are inversely proportional to the amount of mRNA of the gene, and is in a log2 scale. The lines in the "Control" samples correspond to 1, 2 and 3 standard deviations beyond the mean value.

FIGURE 1

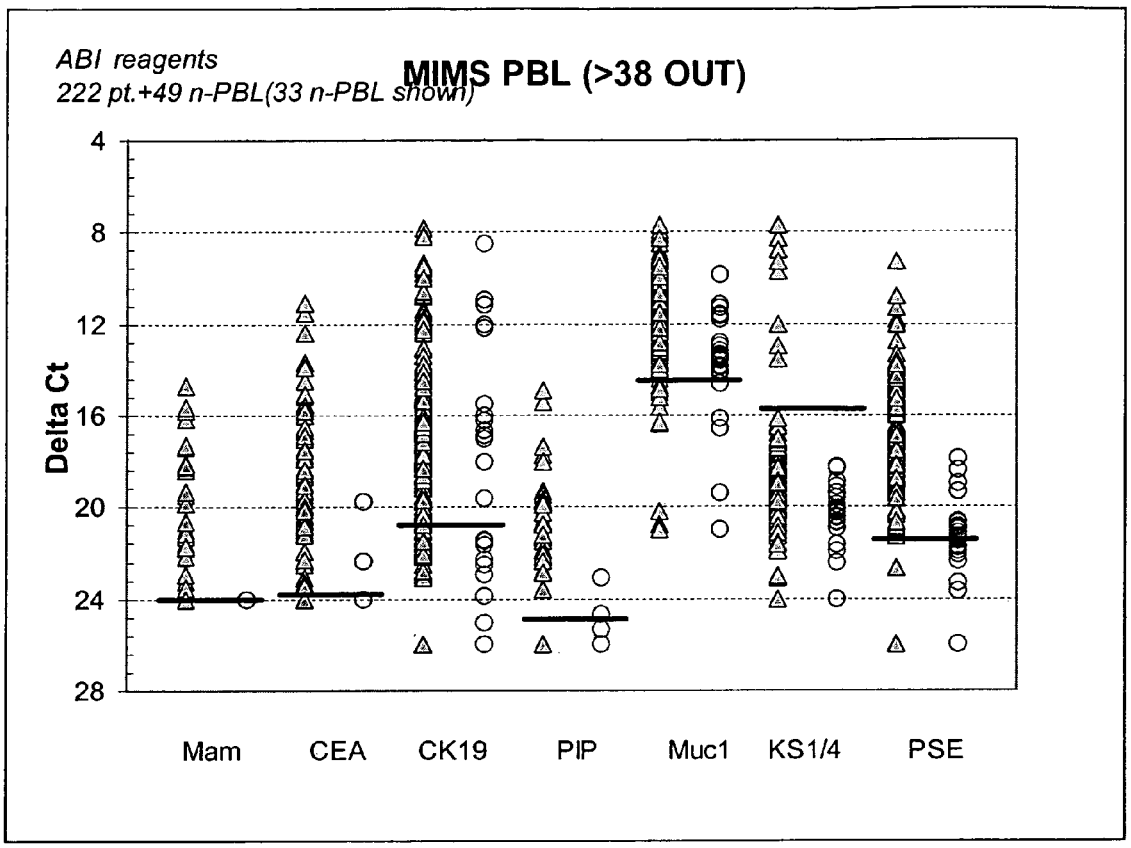

Figure 2. Mam and KS1/4 are overexpressed in peripheral blood obtained from breast cancer patients. Expression levels of the indicated genes were measured in peripheral blood obtained from patients with breast cancer (n=222; triangles) and from control subjects with no evidence of cancer (n=49; circles). Real-time RT-PCR studies were performed in triplicate using b2-microglobulin as the internal reference control gene. Lines correspond to 3 standard deviations beyond the mean of normal controls. For the mam gene, none of 49 of the control samples was positive (0%), whereas 29 of 222 (13%) of the breast cancer samples were positive. For KS1/4, 8 of the breast cancer samples were positive (3.6%), while none of the controls were positive.

FIGURE 2

METHODS AND COMPOSITIONS FOR DIAGNOSING EPITHELIAL CELL CANCER

This application claims priority to U.S. provisional application No. 60/526,759 filed on Dec. 2, 2003. The aforementioned application is herein incorporated by this reference in its entirety.

Certain aspects of the present disclosure were supported by grant or Contract Numbers: DOD N00014-99-1-0784 and DOD SP0007 (MM), and NCI/NIH R21 CA97875-01 (MBW). The Government has some rights in the invention.

BACKGROUND OF THE INVENTION

Field of the Invention

The invention relates to the use of multiple markers detected using RT-PCR to detect metastasis of epithelial cell cancer. The invention further relates to the use of multiple markers to determine cancer staging and prognosis.

SUMMARY OF THE INVENTION

Provided is a method for detecting metastases of epithelial cancers, comprising detecting in non-primary tissue overexpression of a nucleic acid of KS1/4, the overexpression of a nucleic acid of KS1/4 in non-primary tissue being correlated with metastases of epithelial cancers.

Also provided is a method for detecting metastases of epithelial cancers, comprising detecting in non-primary tissue overexpression of a nucleic acid of KS1/4 and overexpression of a nucleic acid of PIP, the overexpression of a nucleic acid of KS1/4 and the overexpression of a nucleic acid of PIP in non-primary tissue being correlated with metastases of epithelial cancers.

Provided is a method for detecting metastases of epithelial cancers, comprising detecting in non-primary tissue overexpression of a nucleic acid of KS1/4 and overexpression of a nucleic acid of mam, the overexpression of a nucleic acid of KS1/4 and the overexpression of a nucleic acid of mam in non-primary tissue being correlated with metastases of epithelial cancers.

Provided is a method for detecting metastases of epithelial cancers, comprising detecting in non-primary tissue overexpression of a nucleic acid of PIP and overexpression of a nucleic acid of mam, the overexpression of a nucleic acid of PIP and the overexpression of a nucleic acid of mam in non-primary tissue being correlated with metastases of epithelial cancers.

Provided is a method for detecting metastases of epithelial cancers, comprising detecting in non-primary tissue overexpression of a nucleic acid of KS1/4, overexpression of a nucleic acid of PIP and overexpression of a nucleic acid of mam, the overexpression of a nucleic acid of KS1/4, the overexpression of a nucleic acid of PIP and the overexpression of a nucleic acid of mam in non-primary tissue being correlated with metastases of epithelial cancers.

Also provided is a method for detecting metastases of epithelial cancers in a subject, comprising detecting in non-primary tissue of the subject overexpression of a nucleic acid of KS1/4 and overexpression of a nucleic acid of lunx, the overexpression of a nucleic acid of KS1/4 and the overexpression of a nucleic acid of lunx in non-primary tissue being correlated with metastases of epithelial cancers in the subject.

BRIEF DESCRIPTION OF THE DRAWINGS

FIG. 1 shows multi-marker real-time RT-PCR analysis of NSCLC. Real-time PCR analyses of EUS-FNA specimens from 10 control MLNs (open squares), 30 cervical control lymph nodes (open circles), EUS-FNA specimens from 9 cytology-positive MLNs (filled circles), and EUS-FNA specimens from 40 cytology-negative MLNs (filled triangles) were performed as described in the text using primer pairs for the indicated genes. Relative levels of gene overexpression were determined from the equation $(1+AE)^{\Delta\Delta Ct}$. Threshold levels of overexpression for each gene were calculated as described in the text and are depicted by the dash located on the right side of each data set.

FIG. 2 shows Marker positivity rates in H&E(−) patients correlates well with log[RLO] values. RLO values for each gene were obtained from Table 1 and are plotted as a function of marker positivity rates in H&E(−) patients (n=344). Data points correspond to filled square (mam); open circle (PIP); filled triangle (mamB); filled circle (CEA): filled diamond (PSE); open square (CK19); open triangle (muc1). Y-values were obtained from population-based statistical analysis of data obtained from MIMS study. Correlation coefficient was obtained using Microsoft excel software. P value was obtained using Fisher's exact test.

programming environment. Area under the curve (AUC) values for each individual marker are included in the figure legend.

Figure 7:
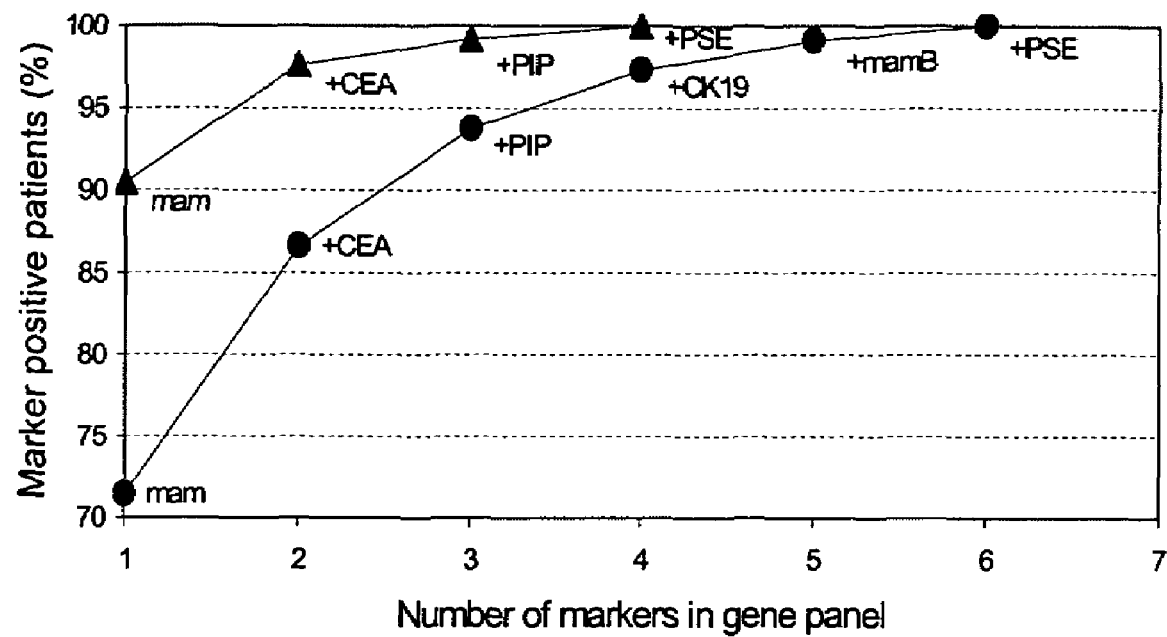

FIG. 7 shows detection of metastatic disease by multimarker RT-PCR. This analysis includes lymph nodes from 126 patients with pathology-positive/marker-positive ALN (filled triangles) and 112 pathology-negative/marker-positive ALN (filled circles). The figure shows the percent of patients positive with gene overexpression detected by real-time RT-PCR using the most frequently expressed gene (mam), and then adding other genes to the marker panel in order of their ability to complement mam, or the existing marker panel. In a separate analysis, using artificial neural networks, the diagnostic accuracy of the multi-marker panel was shown to be significantly better than mam, the most accurate of the individual markers.

Figure 8A:
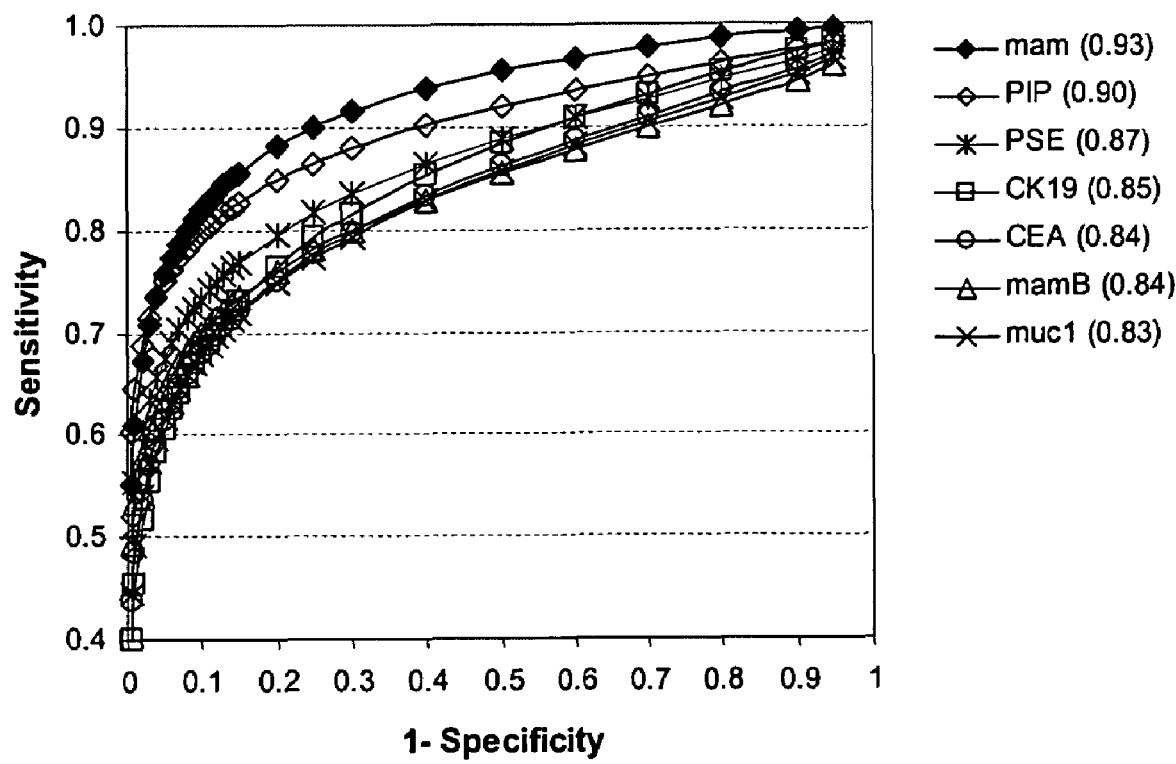
Figure 8B:
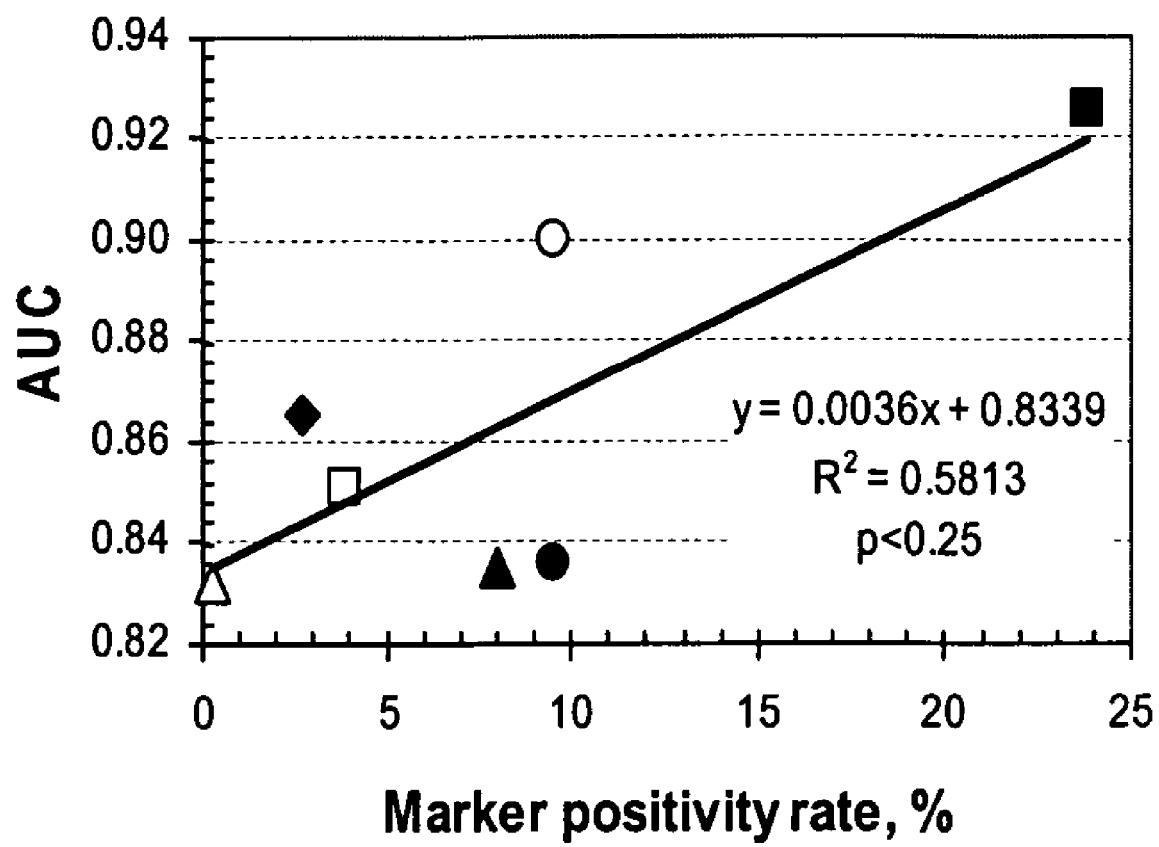

FIG. 8A shows diagnostic accuracy of breast cancer associated genes determined ROC curve analysis. For preliminary marker validation, we performed ROC curve analysis, which is the most commonly used method for assessing the accuracy of diagnostic tests [Henderson, 1993]. The area under the ROC curve (AUC) is a measure of diagnostic accuracy such that values between 0.7 to 0.9 indicate moderate accuracy and values greater than 0.9 indicate high accuracy [Swets, 1988]. For ROC curve analysis, we used Rockit 0.9B Beta Version software [Metz, 1998] and examined 146 H&E(+) axillary lymph nodes from breast cancer patients and 50 negative control cervical lymph nodes. FIG. 8B shows marker positivity rates in H&E (−) patients do not correlate well with AUC values. Marker positivity rates in H&E(−) patients (n=344) were determined using clinical thresholds (3 standard deviations beyond the mean of negative control cervical lymph nodes). A patient was determined to be marker positive if one or more nodes were marker positive. The average number of nodes examined per patient was 2.2. Marker positivity rates shown on the x-axis reflect the percent of total. Data points correspond to filled square (mam); open circle (PIP); filled triangle (mamB); filled circle (CEA): filled diamond (PSE); open square (CK19); open triangle (muc1). No significant correlation between the measured parameters was observed. The fact that AUC values varied over a relatively small range raises the possibility that AUC values may not be sufficiently robust (or sensitive) to allow for critical evaluation of whether a marker is a valid surrogate of micrometastatic disease.

Figure 9A:
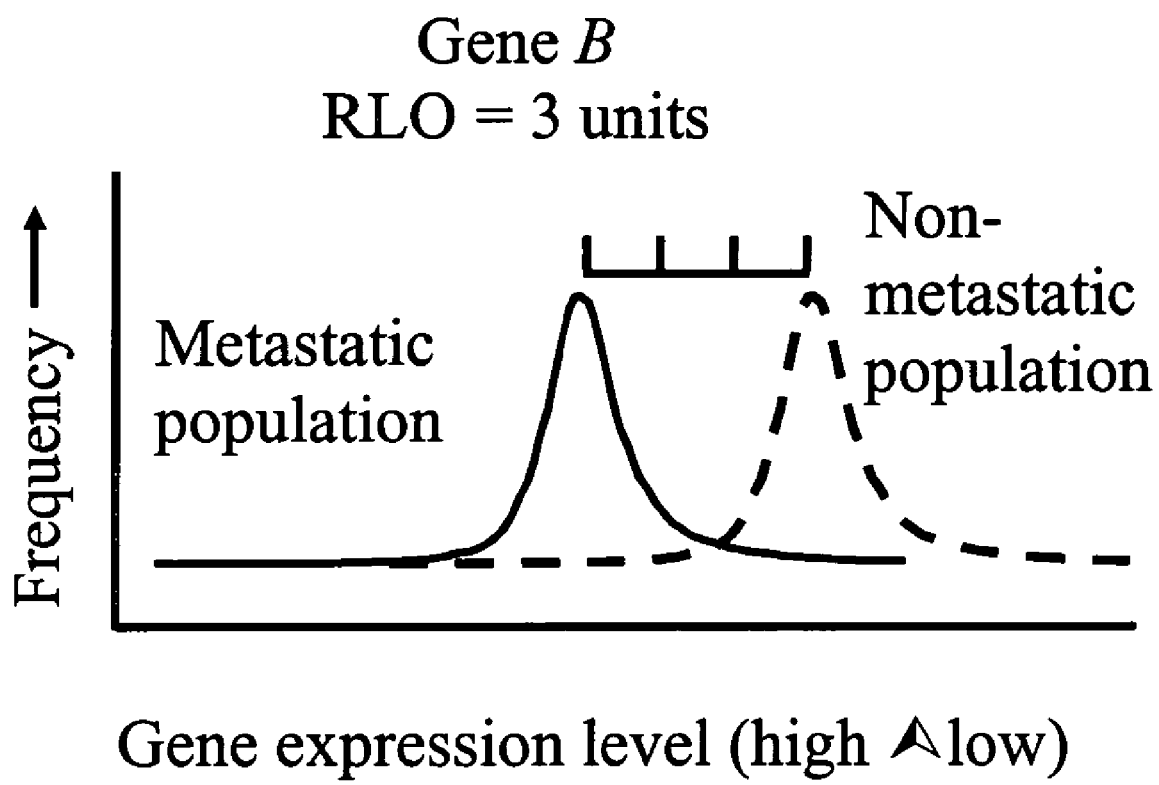
Figure 9B:
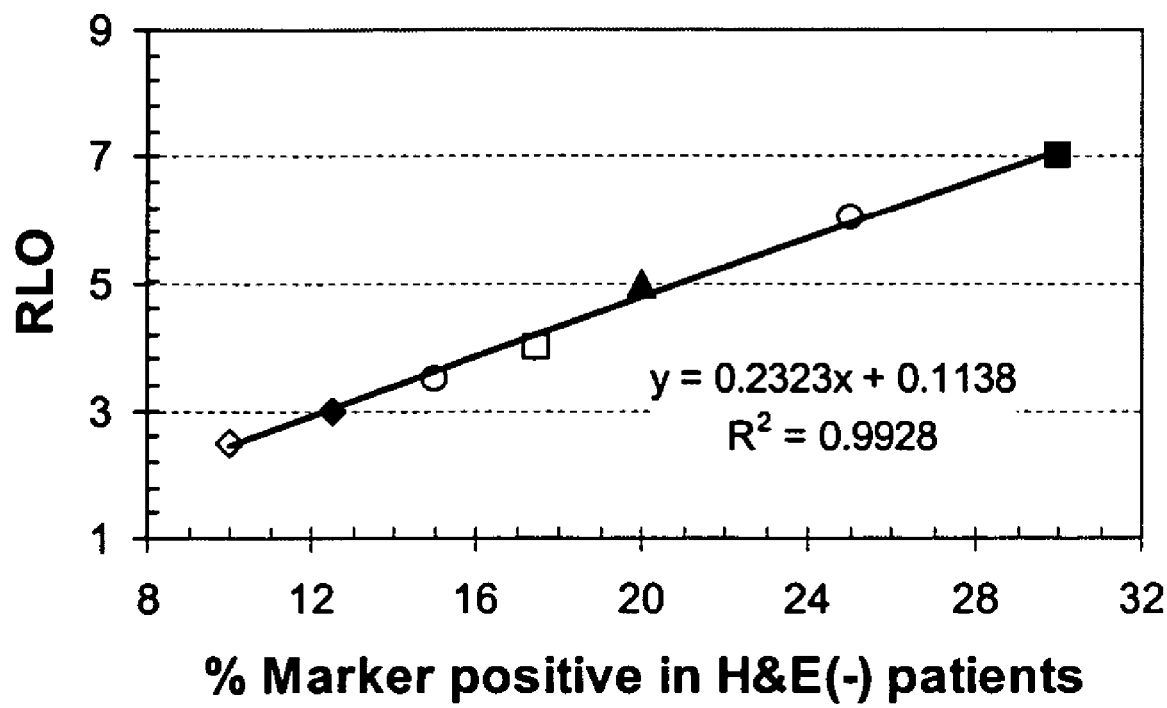
Figure 10A:
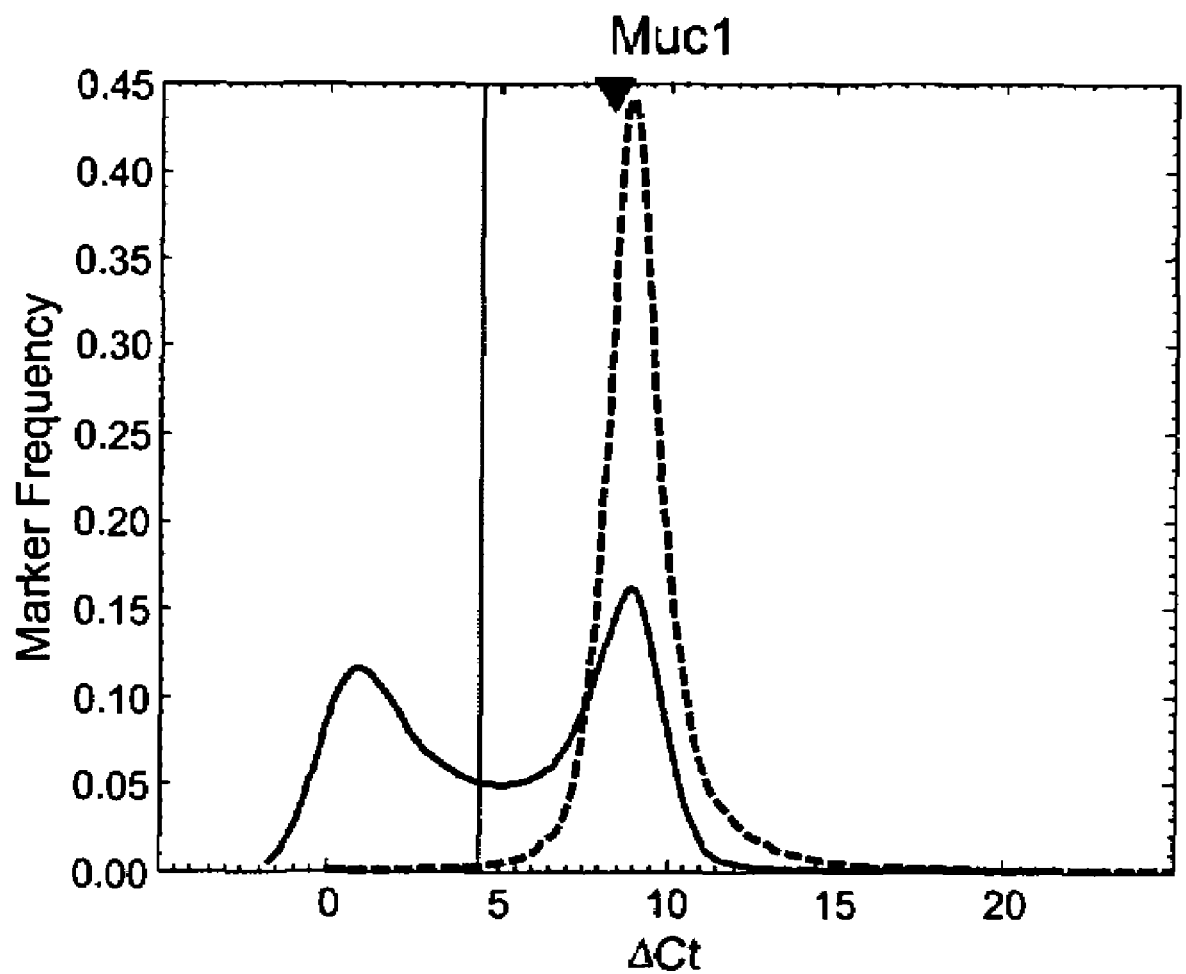
Figure 10B:
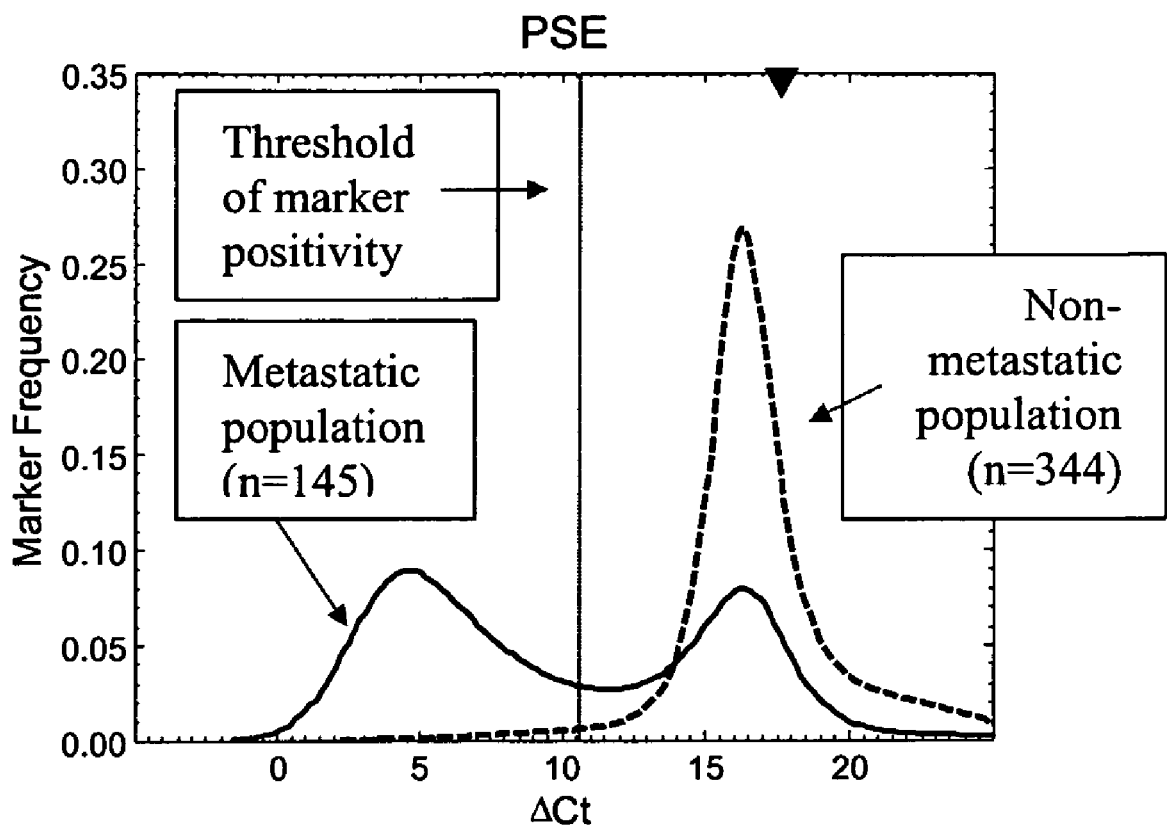
Figure 10C:
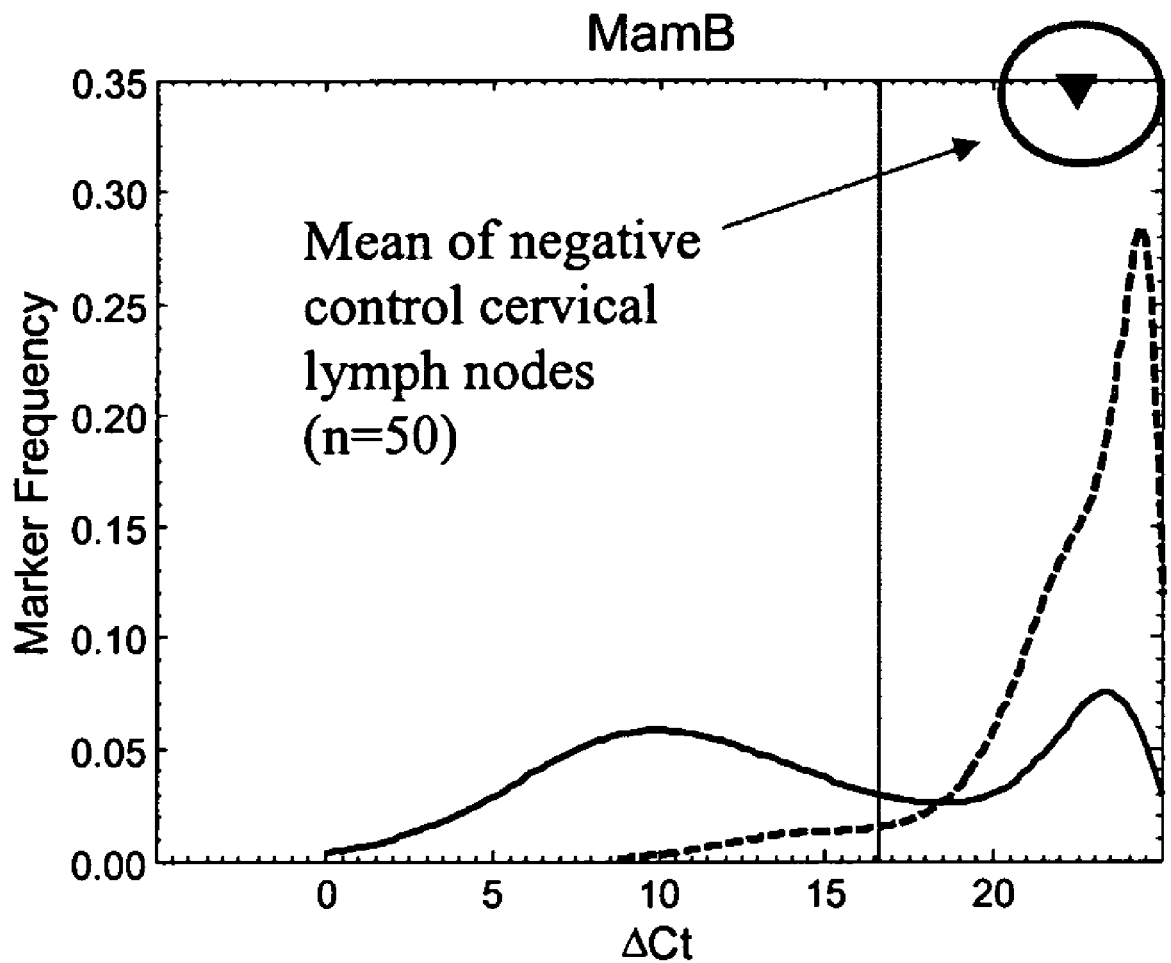
Figure 10D:
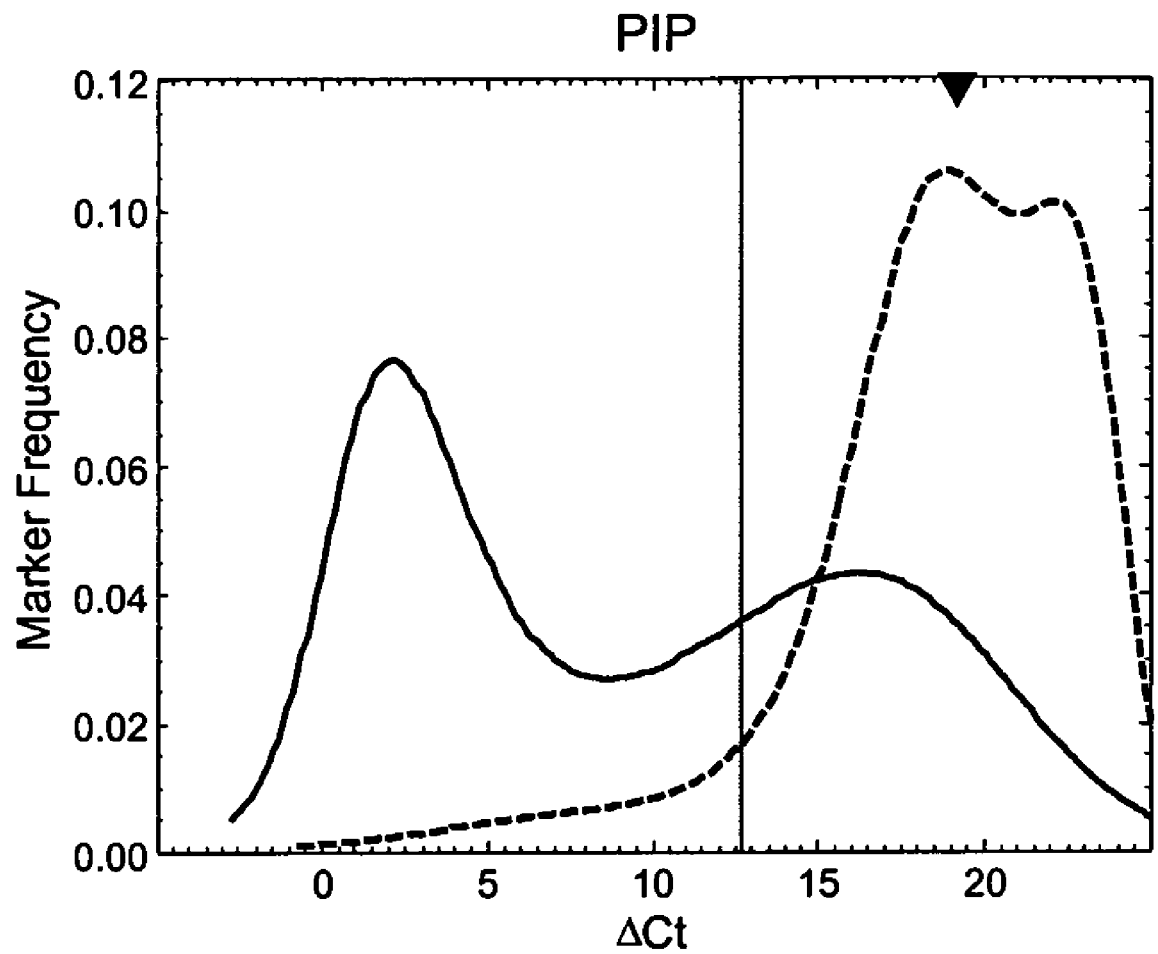
Figure 10E:
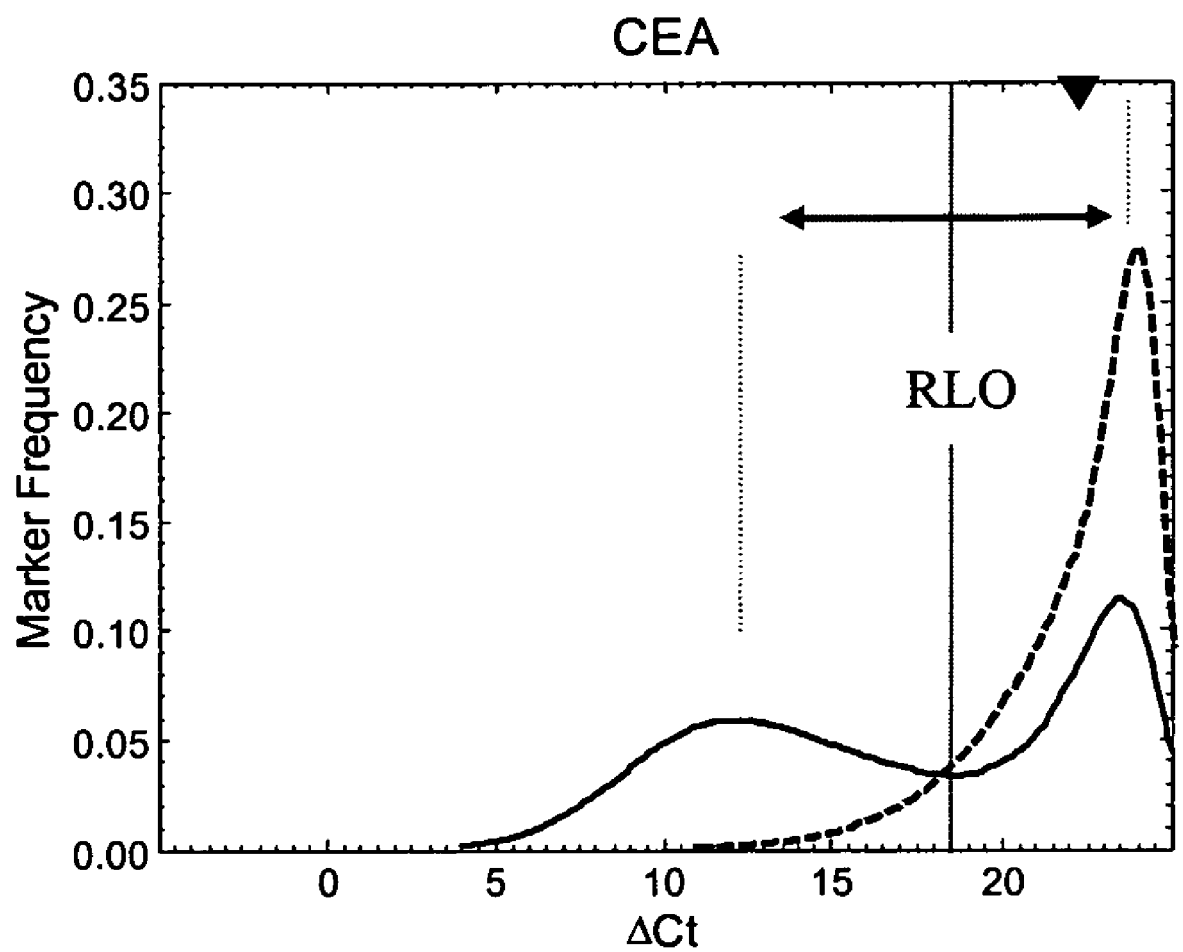
Figure 10F:
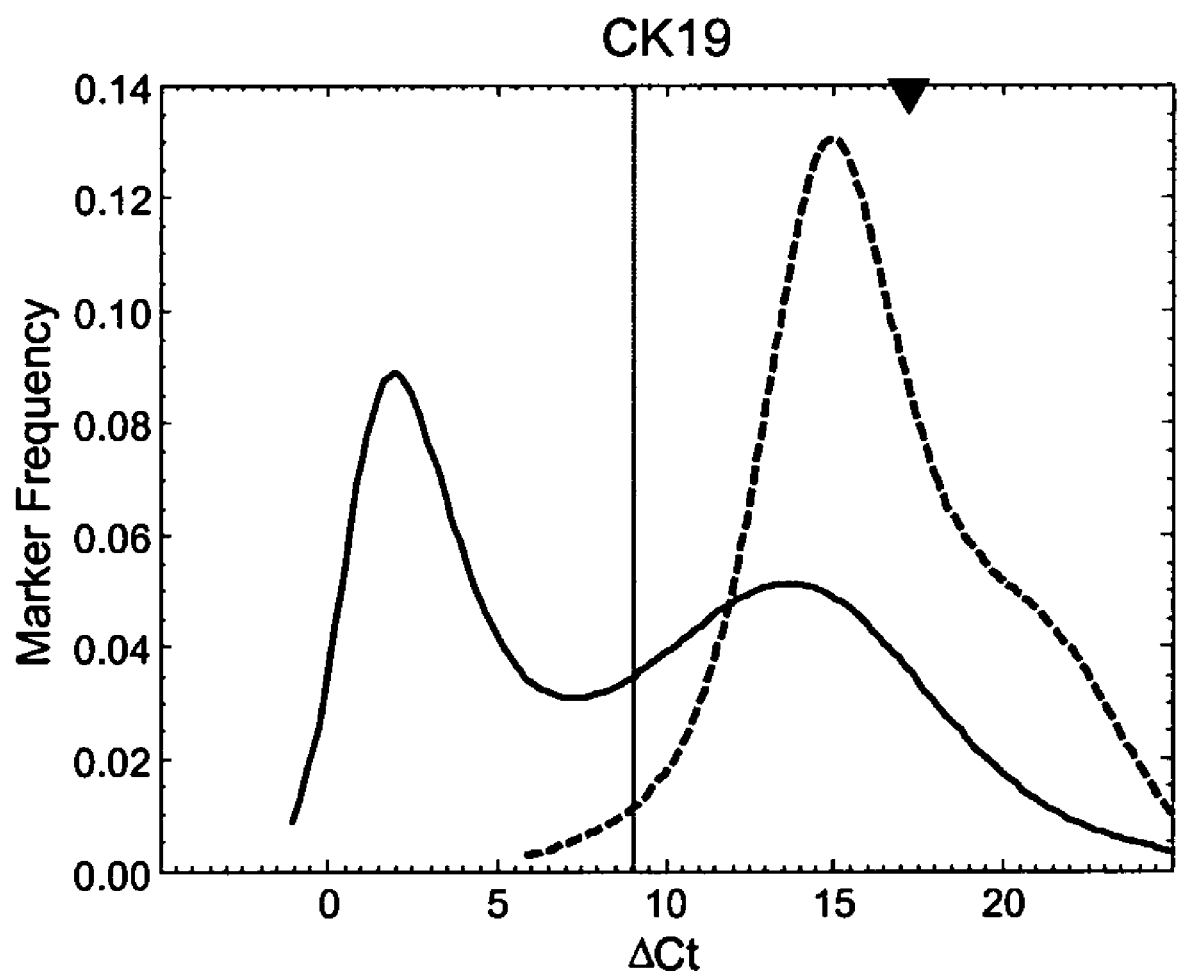
Figure 10G:
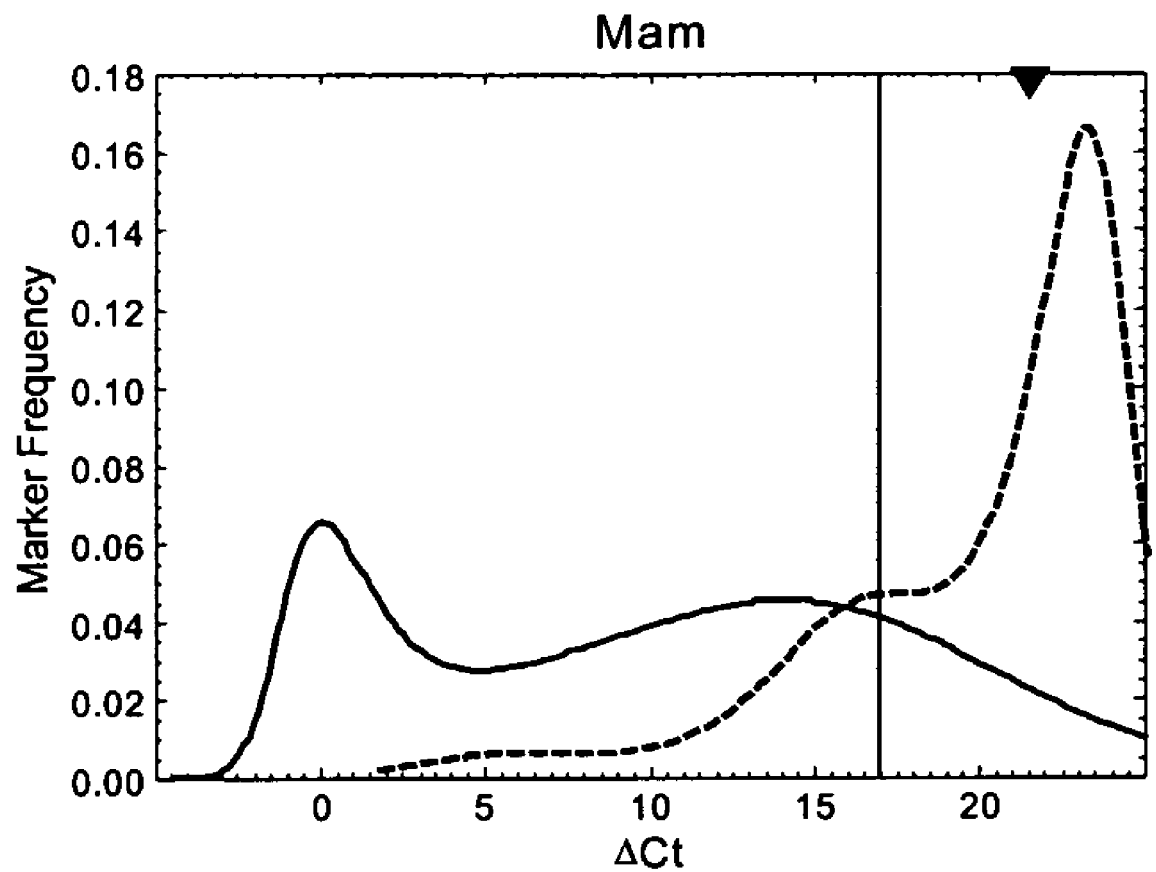

FIGS. 9A-9B show that the rate of micrometastatic disease detection of any reliable surrogate marker must be proportional to its Relative Level of Overexpression (RLO) in metastatic tissue compared to non-metastatic tissue. FIG. 9A shows idealized marker distribution frequency data of hypothetical gene B and plot of various marker RLO values versus marker positivity rates shown in FIG. 9B.

FIGS. 10A-10G show that frequency distributions of the indicated genes were generated using MATLAB 6.5® software (R13, MathWorks, Inc., Natick, Mass.) for H&E(+) (n=145' solid trace) and H&E(−) (n=344; dashed trace) samples. ΔCt values correspond to levels of expression of the gene indicated at the top of each figure; these values are reported in a log2 scale and are relative to an internal reference control gene [4].

Figure 11:
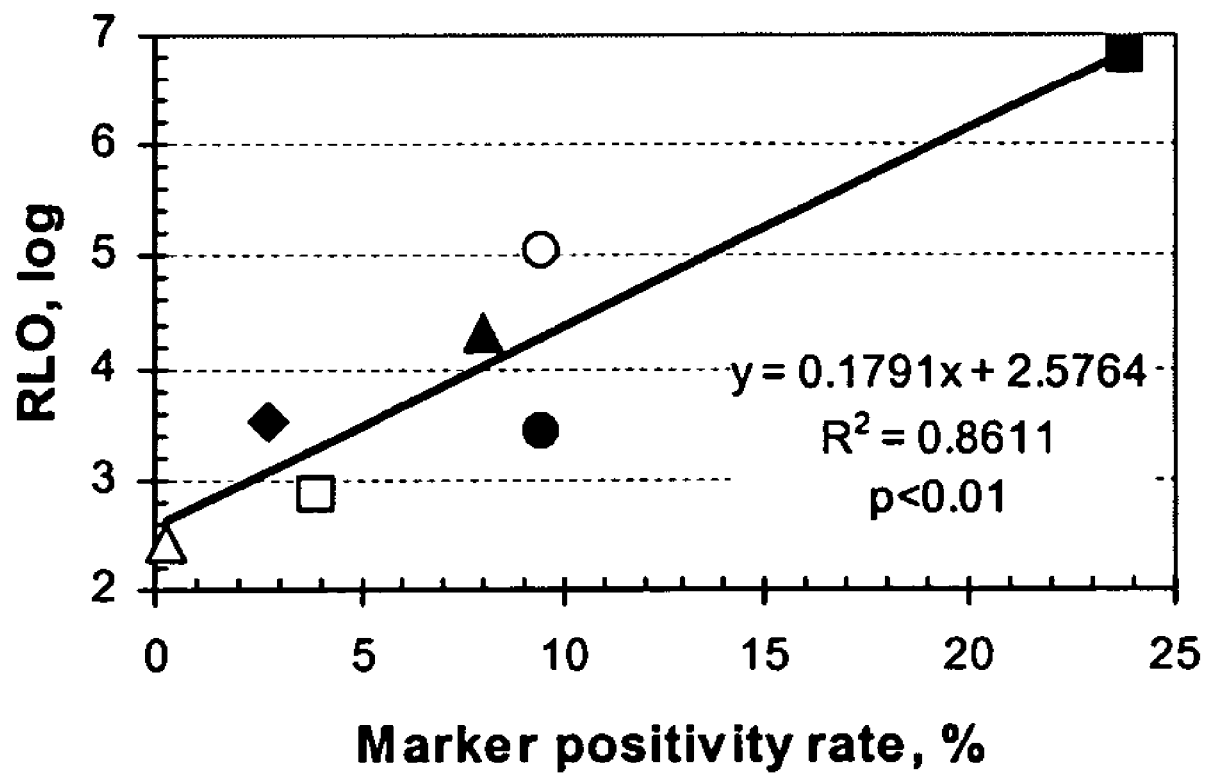

FIG. 11 shows that marker positivity rates in H&E(−) patients correlate well with log [RLO] values. RLO values for each gene were obtained from Table 9 and are plotted as a function of marker positivity rates in H&E(−) patients (n=344). Data points correspond to filled square (mam); open circle (PIP); filled triangle (mamB); filled circle (CEA): filled diamond (PSE); open square (CK19); open triangle (muc1). Correlation coefficient was obtained using Microsoft excel software. P value was obtained using Fisher's exact test.

DESCRIPTION OF THE INVENTION

Provided is an assay using single markers or a combination of markers that allows the determination of whether an individual has an epithelial-derived cancer.

As used in the specification and the appended claims, the singular forms "a," "an" and "the" include plural referents unless the context clearly dictates otherwise. Thus, for example, reference to "a nucleic acid" includes mixtures of two or more such nucleic acids, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that these data, represent endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

A "subject" is an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human.

"Non-primary or secondary tissue" is tissue in which the cancer did not first arise and to which the cancer metastasized, or spread, from the primary tissue.

As used herein, "overexpression" means expression greater than the expression detected in normal, non-cancerous tissue. For example, a nucleic acid that is overexpressed may be expressed about 1 standard deviation above normal, or about 2 standard deviations above normal, or about 3 standard deviations above the normal level of expression. Therefore, a nucleic acid that is expressed about 3 standard deviations above a normal, control level of expression (as determined in non-cancerous tissue) is a nucleic acid that is overexpressed.

Biological samples from a subject containing breast, lung, pancreatic, and esophageal cancer have elevated levels of KS1/4 gene expression. These cancers also have elevated levels of expression of other genes, including mam, PIP and lunx.

Provided is a method for detecting micrometastases (occult metastases/metastases) of epithelial cancers in a subject, comprising detecting in non-primary/secondary tissue of the subject overexpression of a nucleic acid of KS1/4, the overexpression of a nucleic acid of KS1/4 in non-primary/secondary tissue being correlated with micrometastases (occult metastases/metastases) of epithelial cancers in the subject.

Also provided is a method for detecting micrometastases (occult metastases/metastases) of epithelial cancers in a subject, comprising detecting in non-primary/secondary tissue of the subject overexpression of a nucleic acid of KS1/4 and overexpression of a nucleic acid of PIP, the overexpression of a nucleic acid of KS1/4 and the overexpression of a nucleic acid of PIP in non-primary/secondary tissue being correlated with micrometastases (occult metastases/metastases) of epithelial cancers in the subject. An example of an epithelial cancer detected by the disclosed method is breast cancer.

Provided is a method for detecting micrometastases (occult metastases/metastases) of epithelial cancers in a subject, comprising detecting in non-primary/secondary tissue of the subject overexpression of a nucleic acid of KS1/4 and overexpression of a nucleic acid of mam, the overexpression of a nucleic acid of KS1/4 and the overexpression of a nucleic acid of mam in non-primary/secondary tissue being correlated with micrometastases (occult metastases/metastases) of epithelial cancers in the subject. An example of an epithelial cancer detected by the disclosed method is breast cancer.

Also provided is a method for detecting micrometastases (occult metastases/metastases) of epithelial cancers in a subject, comprising detecting in non-primary/secondary tissue of the subject overexpression of a nucleic acid of PIP and overexpression of a nucleic acid of mam, the overexpression of a nucleic acid of PIP and the overexpression of a nucleic acid of mam in non-primary/secondary tissue being correlated with micrometastases (occult metastases/metastases) of epithelial cancers in the subject. An example of an epithelial cancer detected by the disclosed method is breast cancer.

Further provided is a method for detecting micrometastases (occult metastases/metastases) of epithelial cancers in a subject, comprising detecting in non-primary/secondary tissue of the subject overexpression of a nucleic acid of KS1/4, overexpression of a nucleic acid of PIP and overexpression of a nucleic acid of mam, the overexpression of a nucleic acid of KS1/4, the overexpression of a nucleic acid of PIP and the overexpression of a nucleic acid of mam in non-primary/secondary tissue being correlated with micrometastases (occult metastases/metastases) of epithelial cancers in the subject. An example of an epithelial cancer detected by the disclosed method is breast cancer.

Also provided is a method for detecting metastases of epithelial cancers in a subject, comprising detecting in non-primary tissue of the subject overexpression of a nucleic acid of KS1/4 and overexpression of a nucleic acid of lunx, the overexpression of a nucleic acid of KS1/4 and the overexpression of a nucleic acid of lunx in non-primary tissue being correlated with metastases of epithelial cancers in the subject. An example of an epithelial cancer detected by the disclosed method is lung cancer.

In the disclosed methods, the epithelial cancer is selected from the group consisting of breast; bladder, colon; esophageal; pancreatic; prostate, head and neck; skin, including basal cell carcinoma and squamous cell carcinoma; stomach; calcifying epithelial odontogenic tumor (CEOT); carcinoma, epithelial-myoepithelial (EMC); dysembryoplastic neuroepithelial tumor (DNT); epithelial cancer, ovarian (EOC); epithelial tumor, appendiceal; epithelial tumor, oral cavity; spindle epithelial tumour with thymus-like element; thymoma, malignant, medullary epithelial predominant/spindle cell; peritoneal; endometrial; hepatocellular carcinoma; uterine carcinoma; malignant mesothelioma; and malignant thymoma.

In the disclosed methods, the non-primary/secondary tissue can be axillary lymph node, sentinel lymph node, mediastinal lymph node, other lymph nodes, bone marrow, or peripheral blood. Furthermore, because the present data show the correlation of the overexpression of certain markers in non-primary cancer tissue with metastasis of the cancer, the invention provides a method of detecting metastasis to other tissues. For example, bone marrow (e.g., aspirates), blood, bone and adipose tissue, among others, can be tested for the overexpression of the markers described herein, as well as for other markers that become associated with breast cancer. Similarly, other nucleic acids that are now known to be associated with epithelial cell cancer, or are later found to be associated with epithelial cancer, can be used in the methods described herein. These tissues can be isolated using any available method including the methods disclosed herein Provided is a composition comprising a pair of primers specific for KS1/4. Also provided is a composition comprising a pair of primers specific for mam, a pair of primers specific for KS1/4 and a pair of primers specific for PIP. Also provided is a composition comprising a pair of primers specific for mam and a pair of primers specific for KS1/4. Also provided is a composition comprising a pair of primers specific for KS1/4 and a pair of primers specific for PIP. Also provided is a composition comprising a pair of primers specific for mam and a pair of primers specific for PIP. The primer pair specific for mam can, for example, comprise or consist of the polynucleotide set forth in SEQ ID NO:1 and the polynucleotide set forth in SEQ ID NO:2. The primer pair specific for KS1/4 can, for example, comprise or consist of the polynucleotide set forth in SEQ ID NO:3 and the polynucleotide set forth in SEQ ID NO:4. The primer pair specific for PIP can, for example, comprise or consist of the polynucleotide set forth in SEQ ID NO:5 and the polynucleotide set forth in SEQ ID NO:6. Other primers capable of specifically amplifying the markers of the invention can be used in the methods and compositions provided. Methods of designing and testing additional primers are available to the skilled person.

Polynucleotides for use as amplification primers or as probes are provided. A polynucleotide comprising and a polynucleotide consisting of a sequence as set forth in SEQ ID NO:1 is provided. A polynucleotide comprising and a polynucleotide consisting of a sequence as set forth in SEQ ID NO:2 is provided. A polynucleotide comprising and a polynucleotide consisting of a sequence as set forth in SEQ ID NO:3 is provided. A polynucleotide comprising and a polynucleotide consisting of a sequence as set forth in SEQ ID NO:4 is provided. A polynucleotide comprising and a polynucleotide consisting of a sequence as set forth in SEQ ID NO:5 is provided. A polynucleotide comprising and a polynucleotide consisting of a sequence as set forth in SEQ ID NO:6 is provided.

A kit is provided, comprising a polynucleotide selected from the group consisting of SEQ ID NO:3 and SEQ ID NO:4, wherein the kit can comprise SEQ ID NO:1, SEQ ID NO:2, SEQ ID NO:3, SEQ ID NO:4, SEQ ID NO:5 and SEQ ID NO:6. A kit comprising a polynucleotide comprising a sequence selected from the group consisting of SEQ ID NO:1, SEQ ID NO:2, SEQ ID NO:3, SEQ ID NO:4, SEQ ID NO:5 and SEQ ID NO:6 is provided. The kit can contain any one or more of the listed polynucleotides along with any other primers needed to perform an amplification of one of the target nucleic acids disclosed.

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR. It is understood that in certain embodiments, the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

The polynucleotides (primers or probes) can comprise the usual nucleotides consisting of a base moiety, a sugar moiety and a phosphate moiety, e.g., base moiety—adenin-9-yl (A), cytosin-1-yl (C), guanin-9-yl (G), uracil-1-yl (U), and thymin-1-yl (T); sugar moiety—ribose or deoxyribose, and phosphate moiety—pentavalent phosphate. They can also comprise a nucleotide analog, which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. The polynucleotides can contain nucleotide substitutes which are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the target gene typically will be used to produce an amplified DNA product that contains a region of the target gene or the complete gene. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The nucleic acids, such as the oligonucleotides to be used as primers, can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein and nucleic acid molecules can be made using known methods such as those described by Nielsen et al., *Bioconjug. Chem.* 5:3-7 (1994).

The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23)12997-302 (1997), incorporated herein by reference.

Disclosed are chips, for example microarray chips, where at least one address is a sequence or part of a sequence set forth in any of the nucleic acid sequences disclosed herein. For example, the chip can contain a probe for KS1/4, mam or PIP or any combination thereof.

Therefore, provided herein is an array comprising a substrate having a plurality of addresses, wherein each address comprises a capture probe that specifically binds under stringent conditions a nucleic acid of KS1/4, mam, or PIP or to a complement thereof. A nucleic acid bound by the capture probe of each address is unique among the plurality of addresses.

As used herein, "stringent conditions" refers to the washing conditions used in a hybridization protocol. In general, the washing conditions should be a combination of temperature and salt concentration chosen so that the denaturation temperature is approximately 5-20° C. below the calculated Tm of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The Tm of such an oligonucleotide can be estimated by allowing 2° C. for each A or T nucleotide, and 4° C. for each G or C. For example, an 18 nucleotide probe of 50% G+C would, therefore, have an approximate Tm of 54° C. Stringent conditions are known to one of skill in the art. See, for example, Sambrook et al. (2001). An example of stringent wash conditions is 4×SSC at 65° C. Highly stringent wash conditions include, for example, 0.2×SSC at 65° C.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences of a plurality of markers, for example the markers KS1/4, mam, or PIP. The substrate can be any substrate to which polynucleotide probes can be attached including, but not limited to, glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593, 839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Tissue samples can be treated to form single-stranded polynucleotides, for example, by heating or by chemical denaturation, as is known in the art. The single-stranded polynucleotides in the tissue sample can then be labeled and hybridized to the polynucleotide probes on the array. Detectable labels which can be used include, but are not limited to, radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

Disclosed herein are kits that are drawn to reagents that can be used in practicing the methods disclosed herein. The kits can include any reagent or combination of reagents discussed herein or that would be understood to be required or beneficial in the practice of the disclosed methods. For example, the kits could include primers to perform the amplification reactions described, as well as the buffers and enzymes required to use the primers as intended. For example, disclosed is a kit for assessing a subject's risk for cancer metastasis, comprising any one or more of the oligonucleotides set forth in SEQ ID NOs:1-6. The kit can include instructions for using the reagents described in the methods disclosed herein.

Having provided a means for staging cancer based on the overexpression of certain markers, the invention allows for more accurate staging of cancers than current techniques allow. In contrast to the standard method of staging cancer, which relies on histopathologic detection of cancer in the lymph nodes (in combination with primary tumor size and the presence or absence of cancer elsewhere in the body), the detection of markers as taught in the present invention is more sensitive, and thus, more accurate. As shown herein, the overexpression of certain markers or combinations of markers is indicative of a later stage of cancer than was determined using the standard, histopathology-based methods. The present RT-PCR methodology provides valuable prognostic information which allows the clinician to make more informed adjuvant therapy decisions. Thus, the improved information about the stage of a patient's cancer provided by the present methods can be used to tailor a treatment regimen to that patient, increasing the likelihood of improved outcome.

The present method can be used to test paraffin embedded tissues by PCR. These tissues may be from patients currently showing no sign of metastasis according to the usual clinical methods. Thus, testing of the paraffin samples of these patients may be used to inform the doctor and patient of undetected metastasis or the likelihood of later relapse. This method also permits the use of PCR to detect metastasis in specimens that are prepared for the standard histopathologic analysis.

The following examples are put forth so as to provide those of ordinary skill in the art with a complete disclosure and description of how the compounds, compositions, articles, devices and/or methods claimed herein are made and evaluated and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

EXAMPLES

Example 1

Real-Time RT-PCR Detects KS1/4 mRNA in Mediastinal Lymph Nodes From Patients With Non-Small Cell Lung Cancer Non-small cell lung cancer (NSCLC) is the most common cancer-related cause of death for both men and women in the United States. Standard therapies for patients with NSCLC include surgery, chemotherapy and radiation therapy, and the stage of disease dictates choice of therapy. The current staging system for lung cancer uses the American Joint Committee on Cancer TNM system, and its goal is to classify patients into groups based on the extent of disease. This system relies heavily on the pathologic evaluation of the primary tumor (T), regional nodes (N) and distant metastases (M). Patients in whom mediastinal lymph nodes (MLNs) are involved (N2 or N3) are classified with stage III disease [1] and are generally considered inoperable.

Real-time RT-PCR provides sensitive and specific ways to analyze MLNs. In addition, molecular biology approaches using real-time RT-PCR are well suited to the analysis of lymph node tissue procured through minimally invasive procedures such as endoscopic ultrasound-guided fine needle aspiration (EUS-FNA). This technique enables reliable biopsy of MLNs without the need for general anesthesia or surgery [5]. Given the advantages of EUS-FNA, the possibility that metastatic disease could be reliably detected in MLNs of NSCLC patients by real-time RT-PCR was investigated.

To define the ability of real-time RT-PCR to detect metastatic NSCLC in MLNs, nine MLNs containing metastatic NSCLC (5 adenocarcinomas, 1 large cell carcinoma, 1 squamous cell carcinoma, and 2 uncharacterized carcinomas) were procured by EUS-FNA. For negative control, 30 cervical lymph nodes obtained by surgical resection were collected.

For EUS-FNA, a fine needle apparatus commercially produced for use with EUS (EUS N-1, Wilson Cook Co., Winston Salem N.C.) was advanced into a target lymph node under high frequency (7.5 mHz) ultrasound guidance. An occluding stylet within the needle lumen was used to minimize contamination from pass-through structures and was removed once the needle was in position. As suction was applied using a syringe, the needle was moved to and fro within the lymph node for approximately 2 minutes. This procedure typically retrieved a specimen of pure lymph node cells of approximately 0.5-2 cc. Material from the EUS-FNA was placed on multiple slides. One set of slides was air dried, stained with Diff Quik stain (Mercedes Medical, Sarasota, Fla., USA), and interpreted in the endoscopy suite for specimen adequacy and for the presence or absence of metastatic NSCLC. Another set of slides was fixed in 95% alcohol and stained later with Papanicolaou stain. Criteria for metastatic carcinoma were the presence of one or more cohesive clusters of neoplastic cells with characteristic epithelial morphology, and the presence of numerous lymphocytes in the background. Duplicate samples were placed on ice and taken immediately for RNA processing and real-time RT-PCR.

For molecular markers of NSCLC metastatic disease, the epithelial carcinoma-associated gene KS1/4 [6], lunx [7], (also known as palate, lung and nasal epithelium carcinoma associated (Plunc) gene [8,9], CEA, CK19, and muc1 were tested. $\beta_2$-microglobin was used as an internal reference control gene. Sequences for primers used in this example are listed in Table 1. Primers to KS1/4 and lunx were designed using Primer Express Software (PE Biosystems, Foster City, Calif.). RNA isolation and real-time RT-PCR conditions were as previously described (10), with the exception that 0.1 U UngErase enzyme and 0.25 U AmpliTaq Gold were used per 10 □l reaction. The amplification efficiencies (AE) of KS1/4, lunx, and CEA, were 100%, 100%, and 98%, respectively; they were obtained by using the formula $AE=10^{1/m}-1$ (11), where m=the slope of the line determined from linear regression analysis (Microsoft Excel software) of serial ten-fold dilutions of cDNA prepared from the lung cancer cell line A549. Amplification efficiencies of other genes used in this study were previously determined (10).

For each NSCLC-associated gene, □$C_t$ values for cervical control lymph nodes and cytology-positive (Cy$^+$) MLNs were obtained from triplicate reactions. The □$C_t$ value is the difference between the $C_t$ value for a NSCLC cancer-associated gene and a □2-microglobin internal reference control gene. Relative gene expression levels of the samples were derived from real-time RT-PCR data using the equation $(1+AE)^{\square\square Ct}$ [10], where AE is the amplification efficiency of the gene of interest, and □□Ct is the difference between the mean □$C_t$ value in cervical control lymph nodes and the □$C_t$ value in the respective test sample. □$C_t$ threshold values for marker positivity were set at three standard deviations away from the mean of the cervical control data set (FIG. 1). Of the markers examined, KS1/4 had the highest sensitivity for detection of NSCLC metastatic disease (9/9 samples, 100%). The sensitivities for the other genes are listed in Table 1. There was no apparent difference in expression profiles according to tumor histology (e.g., squamous vs. adenocarcinoma). Lunx was overexpressed in 7/9 samples (Table 1 and FIG. 1); it was not overexpressed in one adenocarcinoma sample and in one uncharacterized NSCLC.

During the EUS-FNA procedure a needle is passed through the esophagus into a MLN. Contamination from the esophagus and other pass-through structures is prevented or minimized by an occluding stylet within the needle lumen, which is removed after the needle is positioned within the lymph node. To verify that gene overexpression observed in the Cy$^+$ samples was not due to an artifact associated with the EUS-FNA procedure itself, gene expression levels for 10 negative control (subcarinal MLNs) EUS-FNA samples were determined (FIG. 1). Control EUS-FNA samples were obtained from 10 consecutive patients who had no history of cancer and who were undergoing endoscopy for other indications (e.g., evaluation of benign pancreato-biliary disease). KS1/4 and lunx were not overexpressed in any of the 10 EUS-FNA negative control samples (i.e., specificity=10/10, or 100%, Table 1), providing evidence that overexpression of these genes in the Cy$^+$ samples was due to metastatic cancer. Regarding the other markers, CK19, CEA, and muc1 were overexpressed in 3, 2, and 1 EUS-FNA control nodes, respectively. These results suggest that overexpression of CK19, CEA, or muc1 can be associated with non-cancer events. The results of our analyses of control and Cy$^+$ EUS-FNA samples show that KS1/4 is the most informative of these molecular markers for NSCLC metastatic disease.

To explore the possibility that real-time RT-PCR might be capable of detecting occult micrometastases, 40 cytology-negative (Cy$^-$) MLNs from 27 NSCLC patients who had no evidence of metastatic disease were analyzed. Overexpression of high specificity markers KS1/4 and lunx was detected in 2/40 and 0/40 Cy$^-$ MLNs respectively. Overexpression of the lower specificity markers muc1, CEA, or CK19 was detected in 2/40, 10/40, and 18/40, Cy⁻ MLNs respectively. These results show that real-time RT-PCR is useful to detect occult NSCLC micrometastatic disease.

In summary, five molecular markers (lunx, KS1/4, CEA, CK19, and muc1) were tested for use with real-time RT-PCR of EUS-FNA specimens, and their sensitivity and specificity for the detection of NSCLC metastases were evaluated. Overexpression of KS1/4 as well as at least one other marker gene was detected in all nine Cy⁺ specimens. The mean number of markers overexpressed was 3.8. Overexpression of lunx or KS1/4 was not detected in any of the control lymph nodes and thus had the highest specificity for NSCLC. These results demonstrate that real-time RT-PCR combined with EUS-FNA has value for staging patients with NSCLC. Further, this is the first study to establish that KS1/4 is an informative molecular marker of metastatic NSCLC, and its apparent diagnostic accuracy is superior to other candidate markers.

sequences and SYBR Green I chemistry. For normalization purposes, an internal reference control gene ($\beta_2$-microglobulin) was also used.

1. Establishment of $\Delta C_t$ threshold values. Diagnostic tests require the establishment of threshold values, such that test values below a given threshold indicate no disease, and test values above a given threshold indicate the presence of disease. Threshold values for each marker were established at three standard deviations above the mean of negative control cervical lymph nodes and are as follows: 16.9 (mam), 12.7 (PIP), and 9.0 (KS1/4). At these threshold values, the specificity of each gene was 100%.
2. Measured sensitivity rates of various marker combinations for samples containing pathologically confirmed disease. Positivity (sensitivity) rates for markers individually or in various combinations are shown in Table 2. For individual markers, high sensitivity rates were observed for KS1/4

TABLE 1

Primer pairs/amplicons analyzed by real-time RT-PCR

| Gene | Sequence of selected primer pair[a] | Amp. length[b] | Pred. $T_m$[c] | Meas. $T_m$[d] | Primer ref. | Sens.[e] | Spec.[f] |
|------|-------------------------------------|-----------------|----------------|----------------|-------------|----------|----------|
| KS1/4 | CGCAGCTCAGGAAGAATGTG (SEQ ID NO:3) TGAAGTACACTGGCATTGACGA (SEQ ID NO:4) | 88 | 77 | 78.6 | This paper | 9/9 | 10/10 |
| lunx | CCCTGGAAGCCTGCAAATT (SEQ ID NO:7) GAACCAACTCAGGCAGGACTT (SEQ ID NO:8) | 110 | 81 | 81.6 | This paper | 7/9 | 10/10 |
| muc1 | ACCATCCTATGAGCGAGTACC (SEQ ID NO:9) GCCACCATTACCTGCAGAAAC (SEQ ID NO:10) | 107 | 83 | 83.1 | [10] | 8/9 | 9/10 |
| CEA | TGTAGCTGTTGCAAATGCTTTAAGAAAGAAGC (SEQ ID NO:11) GGGCCACTGTCGCATCATGATTGG (SEQ ID NO:12) | 131 | 82 | 81.0 | [2] | 6/9 | 7/10 |
| CK19 | CATGAAAGCTGGGTTGGAAGA (SEQ ID NO:13) TGATTCTGCCGCTCACTATCAG (SEQ ID NO:14) | 138 | 84 | 86.3 | [10] | 8/9 | 8/10 |

[a]Forward primer is shown as upper sequence in the respective primer pair. Reverse primer is the lower sequence. All sequences are written 5'→3'.
[b]Length of amplicon in nucleotides.
[c]Predicted $T_m$ as determined using Primer Express software.
[d]Measured $T_m$ as determined from dissociation profile analysis (12).
[e]Sensitivity of respective gene for NSCLC detection in Cy+ samples.
[f]Specificity of gene with respect to negative control EUS-FNA samples.

Example 2

Combination Analysis of Molecular Markers for the Detection of Metastatic and Occult Metastatic Breast Cancer The purpose of this study was to determine the utility of combining two or three molecular markers for sensitive detection of metastatic and occult metastatic (micrometastatic) breast cancer. RNA was isolated from 24 axillary lymph nodes surgically resected from 24 breast cancer patients. Each node was examined by a pathologist and determined to contain metastatic disease on the basis of positive hematoxylin and eosin staining. RNA was copied into cDNA using reverse transcriptase. Expression levels of three cancer-associated genes (mam, PIP, and KS1/4) were determined by real-time RT-PCR measurements using gene-specific primer sequences and SYBR Green I chemistry.

and mam (92% each). For 2-marker combinations, KS1/4+PIP(K+P) or KS1/4+mam (K+M) yielded 100% sensitivity.

TABLE 2

Sensitivity rates of various marker combinations for detection of pathologically confirmed metastatic breast cancer.

| KS1/4 | PIP | Mam | K + P | K + P + M | P + M | K + M |
|-------|-----|-----|-------|-----------|-------|-------|
| 0.92 | 0.63 | 0.92 | 1.00 | 1.00 | 0.92 | 1.00 |

3. Estimated sensitivity rates of various marker combinations for samples containing theoretically reduced disease burden. Data obtained from real-time RT-PCR studies are quantitative in nature. For the data obtained in the above studies, reduced disease burden levels (10%, 1%, and 0.1%) were simulated and marker positivity rates were determined (Table 3). As the disease burden decreased, the predicted sensitivity of the KS1/4 marker decreased dramatically (down to 0% for 0.1% metastatic disease burden; Table 3). For the theoretical 1% disease burden, a two-marker combination of KS1/4+mam was the most sensitive, whereas for 0.1%, PIP+mam was the most sensitive.

TABLE 3

Sensitivity of marker combinations for detection of theoretical amounts of metastatic breast cancer.

| Disease burden | KS1/4 | PIP | mam | K + P | K + P + M | P + M | K + M |
|---|---|---|---|---|---|---|---|
| 10% metastatic | 0.54 | 0.63 | 0.71 | 0.79 | 0.83 | 0.71 | 0.83 |
| 1% metastatic | 0.25 | 0.46 | 0.58 | 0.58 | 0.71 | 0.58 | 0.71 |
| 0.1% metastatic | 0.00 | 0.25 | 0.42 | 0.25 | 0.50 | 0.50 | 0.42 |

TABLE 4

Primers for KS1/4, main and PIP

| Gene | Sequence of selected primer pair | Amp. length | Pred. $T_m$ | Meas. $T_m$ | Reference |
|---|---|---|---|---|---|
| KS1/4 | CGCAGCTCAGGAAGAATGTG (SEQ ID NO:3) TGAAGTACACTGGCATTGACGA (SEQ ID NO:4) | 88 | 77 | 78.6 | [13] |
| mam | CGGATGAAACTCTGAGCAATGT (SEQ ID NO:1) CTGCAGTTCTGTGAGCCAAAG (SEQ ID NO:2) | 108 | 75 | 76.0 | [10] |
| PIP | GCCAACAAAGCTCAGGACAAC (SEQ ID NO:5) GCAGTGACTTCGTCATTTGGAC (SEQ ID NO:6) | 89 | 77 | 77.5 | [10] |

TABLE 5

Summary of Genes

| Gene name used in patent application | GenBank designation | GenBank description | GenBank Sequence ID# |
|---|---|---|---|
| KS1/4 | TACSTD1 | tumor-associated calcium signal transducer 1 | NM_002354 |
| PIP | PIP | prolactin-induced protein | NM_002652 |
| mam (mammaglobin) | SCGB1A1 | secretoglobin, family 1A, member 1 (uteroglobin) | NM_003357 |

Conclusions
1. For diagnostic purposes, two-marker combinations of KS1/4+PIP or KS1/4+mam are very sensitive.
2. As disease burden decreases, the diagnostic accuracy of KS1/4 is predicted to decrease at a higher rate compared to PIP or mam.
3. For prognostic purposes (i.e., detection of occult disease), a combination of all three markers is likely required to achieve maximum sensitivity. This conclusion is supported by the results of the MIMS trial (Example 4), in which expression levels of seven cancer-associated genes (mam, mamB, PIP, CK19, muc1, cea, and PSE) were determined in 344 patients with no documented metastatic disease.
4. Based on results obtained from the MIMS trial and the KS1/4 data included herein, the estimated KS1/4 positivity rate in pathology-negative breast cancer patients is estimated at ~7%, a value below that of mam (24%) and PIP (9.5%) (see Appendix).

Clinical Implications

The emergence of high throughput real time PCR capability which can reliably quantitate the amount of template present allows for the establishment of threshold values required for a diagnostic test. There are three applications for this new technology and marker combinations:

Diagnostic Test: The combination of the above breast marker and MIMS clinical trial data (see Example 4) provides evidence that a diagnostic two marker test can be designed using either KS1/4+PIP, PIP mam, or KS1/4+mam that would be able to match current histopathology. Such a test should be cost effective and easily applied given the lack of professional fees involved and the current availability of PCR technology.

Detection of Occult Disease: The data show that there is a significant amount of occult disease not detected by standard pathology. Because of the minimal disease present, a combination of all three markers is particularly useful to achieve maximum sensitivity. This conclusion is supported by results of the MIMS trial. This test is expected to have impact on clinical decision-making and treatment plans for newly diagnosed breast cancer patients. Prognostic Marker Detection: Individual markers or combinations of markers have prognostic implication.

Example 3

Cluster Analysis of Real-Time RT-PCR Data Derived From a Two-Gene Marker Panel (KS1/4 and PSE) Allows for Molecular Diagnosis of Esophageal Adenocarcinoma Although the incidence of squamous cell carcinoma of the esophagus has remained relatively constant in recent years, the incidence of esophageal adenocarcinoma has steadily increased. Barrett's esophagus (BE) is a premalignant condition caused by chronic gastroesophageal reflux, and numerous reports suggest that BE is a precursor lesion for esophageal adenocarcinoma. Elucidation of the molecular biology underlying malignant transformation in BE leads to markers for early detection of carcinomas and enables therapeutic interventions to prevent or treat this otherwise highly lethal neoplasm. In this study, quantitative real-time RT-PCR was used, and the expression levels of seven cancer-associated genes (PSE, KS1/4, ErbB2, POTE, HoxC6, CEA, and SBEM) in 17 adenocarcinomas of the esophagus, 6 normal esophageal tissues, and 2 Barrett's esophagus samples were determined. When EpCam (KS1/4) expression levels were plotted as a function of PSE levels, four unique clusters emerged. Two of the clusters were derived from the adenocarcinoma samples (arbitrarily referred to as Type I and Type II). All normal tissue samples were within the third cluster, while the two BA samples were within a fourth cluster. For the respective adenocarcinoma clusters, the correlation between EpCam and PSE expression levels was 0.996 and 0.651, providing evidence that expression of the two genes are coordinately regulated. Alternatively, PSE (a transcriptional factor of the Ets family) may directly activate expression of EpCam, a gene known to be involved in cell migration and invasion. The results provide evidence that EpCam and PSE are useful diagnostic markers of adenocarcinoma of the esophagus. Further, the protein products of these genes are potential therapeutic targets.

The KS1/4 marker and/or the antibody which recognizes its gene product is known by various names (TROP1, [14]; AUA1, [15]; HeGP314, [16]; CO17-1A, [17]; EpCAM, [18]; MK-1, [19]; M4S1, [20]; EGP40, [21]; EGP2, [22]; TAC-STD1, [20]; KSA, [18]; GA733-2, [23]).

Example 4

Molecular Detection of Micrometastatic Breast Cancer in Pathology-Negative Axillary Lymph Nodes Correlates With Traditional Predictors of Prognosis An Analysis of a Prospective Multi-Institutional Cohort Study Background:

The presence of axillary lymph node metastases remains one of the most valuable prognostic indicators in women with breast cancer. However, the clinical relevance of molecular detection of micrometastatic breast cancer in sentinel lymph nodes (SLN) and non-sentinel axillary lymph nodes (ALN) has not been previously established.

Methods: 489 breast cancer subjects with primary tumor size T1, T2, or T3 were enrolled in a prospective, multi-institutional cohort study. ALN were analyzed by standard histopathology (H&E staining) at each individual institution. A representative sample of the ALN was also analyzed by multimarker real-time RT-PCR analysis (mam, mamB, muc1, CEA, PSE, CK19, PIP) designed to detect breast cancer micrometastases.

Results:

A positive marker signal was observed in 126 of 145 (87%) subjects with pathology-positive ALN, and in 112 of 344 (33%) subjects with pathology-negative ALN. In subjects with pathology-negative ALN, a positive marker signal was significantly correlated with traditional indicators of prognosis, such as histological grade (p=0.0255) and St. Gallen risk category (p=0.022). Mammaglobin was the most informative marker in the panel, accounting for 90.5% and 71.4% of the marker signals in subjects with pathology-positive and pathology-negative ALN, respectively. The combination of mam and CEA yielded the highest sensitivity for metastatic disease detection, accounting for 97.6% of the marker signals in subjects with pathology-positive ALN.

Conclusion:

This is the first report to show that overexpression of breast cancer-associated genes in breast cancer subjects with pathology-negative ALN correlates with traditional indicators of disease prognosis. The results provide strong evidence that molecular markers serve as valid surrogates for the detection of occult micrometastases in ALN.

Introduction

The goal of breast cancer staging is to classify patients by the extent of disease into groups with similar clinical outcomes. Staging facilitates patient management, allowing clinicians to tailor therapies to individual patients. One of the most important prognostic indicators in women with breast cancer is the presence of axillary lymph node (ALN) metastases. Frequently, the presence of ALN metastases is the critical parameter for determining if a breast cancer patient is a candidate for adjuvant systemic chemotherapy or hormonal therapy [24-27]. As a result, staging for newly diagnosed clinical Stage I and II breast cancer patients has traditionally included an ipsilateral axillary lymph node dissection. Unfortunately, standard histopathology analysis of ALN (hematoxylin and eosin staining and microscopic examination) does have limitations. A number of studies have shown that performing multiple sections and/or immunohistochemical staining (IHC) of ALN increases the detection of breast cancer metastases by up to 25% [28-30]. Furthermore, these retrospective analyses suggest that the clinical outcome for patients with these micrometastases is similar to patients with pathology-positive ALN [28,29,31]. Taken together, these findings suggest that the development of more sensitive methods for the detection of micrometastatic breast cancer in ALN is likely to significantly improve breast cancer staging.

The recent identification of genes overexpressed in breast cancer combined with advances in molecular biology provide such an opportunity [32-42]. The reverse transcriptase polymerase chain reaction (RT-PCR) is capable of sensitive detection of metastatic disease in ALN of breast cancer patients [40, 43]. Others have reported that RT-PCR is exquisitely sensitive—capable of detecting one cancer cell per $10^7$ normal cells [44-46]. Ironically, this exquisite sensitivity of RT-PCR may have hindered its clinical application since the majority of potential markers have some level of normal tissue expression [47, 48]. Since conventional RT-PCR techniques are at best semi-quantitative, it has been difficult to differentiate between baseline levels of gene expression in normal tissues and increased levels of gene expression associated with breast cancer [33, 47, 49-56]. As a result, some investigators consider PCR technology to be too problematic for clinical application with false positive and/or clinically irrelevant results a significant concern [33, 47, 49, 51-54, 56-58].

Real-time RT-PCR solves these limitations by using an online fluorescence detection system that precisely quantifies the amount of PCR product. Real-time RT-PCR is able to differentiate between baseline gene expression in normal tissues, and gene overexpression associated with metastatic breast cancer [10, 59]. For example, CEA, CK19 and muc1 have detectable baseline gene expression in normal control lymph nodes, but the gene expression levels in lymph nodes with metastatic breast cancer is 5- to 3500-fold higher [10]. The data indicate that the genes mam, PIP, PDEF, CK19, CEA, muc1, and mamB have particular promise for the detection of metastatic breast cancer [40, 10, 59]. Furthermore, the data indicate that a combination of multi-marker analysis and quantitative real-time RT-PCR is a precise and powerful tool for the detection of breast cancer metastases in ALN [10].

Although these results suggest that molecular markers could serve as valid surrogates for the presence of metastatic and micrometastatic breast cancer, the clinical relevance of these molecular diagnostic assays remains to be defined. The Minimally Invasive Molecular Staging of Breast Cancer Trial (MIMS) is the first prospective cohort study to apply multi-marker real-time RT-PCR to the detection of breast cancer micrometastastes in ALN. Sentinel or non-sentinel ALN from 489 breast cancer subjects with primary tumor size T1, T2, or T3 were analyzed by standard histopathology and by multi-marker real-time RT-PCR analysis (mam, mamB, muc1, CEA, PSE, CK19, PIP). The study was designed with sufficient statistical power to correlate molecular analyses with clinical outcome (the power calculation was based on the assumption that clinical outcome will be measured in terms of the proportion of subjects having disease relapse within five years of diagnosis). It was determined that real-time RT-PCR is very sensitive for the detection of metastatic breast cancer in ALN and that overexpression of breast cancer-associated genes in subjects with pathology-negative ALN, is correlated with traditional indicators of poor prognosis.

Materials and Methods

Study Design.

A prospective cohort study design was adopted where, upon recruitment, eligible participants with Stage I, IIa or IIb breast cancer were requested to consent to tissue sampling from ALN, SLN, bone marrow, and whole blood. Tissue sampling was accomplished during the planned surgical procedure while the subject was under anesthesia. Real-time RT-PCR analyses were performed on all tissue specimens submitted to the Central Molecular Diagnostics Laboratory. Staging was performed according to the standard guidelines established by the American Joint Committee on Cancer (AJCC), and included the results of routine histopathology of ALN, but not the real-time RT-PCR results. The real-time RT-PCR analyses were performed blinded to the pathology results. Treatment followed the current standard of care without the knowledge of, or reference to, the molecular analyses. The Clinical Innovation Group served as the coordinating center, and all study data were collected, processed and analyzed at this central facility.

Data Management.

Case report forms (CRFs) indexed by a unique subject number were used to record the clinical data for research purposes. The site investigators maintained the key that linked subject number with subject name to ensure confidentiality of the data at the coordinating center. Once CRFs were completed, they were transmitted via express mail to the coordinating center for processing. The CRFs were independently double key entered into a Clintrial 4.2 database. The database was programmed with consistency checks to ensure the data entered were within a valid range, logical sequences were followed, and that all required items were completed. If deficiencies in the data were identified, written data clarification requests were sent to the sites to update the information. Quality control of the data was conducted in two phases. Trained monitors verified reported data against source documents (i.e., monitored) and ensured all applicable regulatory documents were current. An additional quality control step was conducted by randomly sampling 20% of CRFs in the database for a CRF-to-database audit. Both processes include written documentation of discrepancies identified.

Study subjects.

550 subjects with pathologically confirmed invasive breast carcinoma were enrolled in the MIMS Trial. Inclusion criteria were: age 18 and older, tumor size category of T1-T3, ECOG (Eastern Cooperative Oncology Group) performance status: 0 (normal), 1 (with symptoms but ambulatory), or 2 (in bed <50% of the time), recent bilateral mammogram with normal contralateral breast, and chest X-ray with no evidence of metastatic breast cancer. Exclusion criteria were: inflammatory breast cancer or Paget's Disease, ductal carcinoma in situ (DCIS) without evidence of invasive cancer, clinical evidence of supraclavicular, infraclavicular or axillary lymph node involvement, or known metastatic disease. Subjects with a history of previous treatment for breast cancer were also excluded. Informed consent was obtained in accordance with each participating center's institutional review board regulations.

ALN specimens from breast cancer subjects.

The surgeon and surgical pathologist at the individual clinical centers selected the ALN for the study. In general, if a sentinel lymph node (SLN) biopsy was performed, the sentinel lymph node was submitted, although this was not required. If an ALN dissection was performed, at least three ALN were submitted. Approximately one-half of the selected SLN and ALN were sent to surgical pathology at the clinical center for routine histopathology. The other half of the selected ALN were snap-frozen in liquid nitrogen and shipped to the Central Molecular Diagnostics Laboratory on dry ice for real-time RT-PCR analyses. ALN were evaluated by standard hematoxylin and eosin (H&E) histopathology at the participating center. The pathology status for lymph nodes was based on the H&E staining only; if IHC was performed and the ALN was positive only by IHC, the subject was considered to have pathology-negative ALN. Real-time RT-PCR analyses were performed blinded to the results of the standard histopathology and IHC (if performed).

Lymph node specimens from control subjects without evidence of malignancy.

In order to define baseline expression levels for the molecular markers used in this study, normal lymph nodes from patients without evidence of malignancy were obtained in a tissue acquisition study separate from the MIMS Trial. Informed consent was obtained from 51 patients undergoing elective carotid endarterectomy at the Medical University of South Carolina. None of the patients had a history or clinical evidence of malignancy. At the time of the procedure, a single cervical lymph node was removed, snap-frozen in liquid nitrogen and sent to the Central Molecular Diagnostics Laboratory for real-time RT-PCR analyses.

RNA isolation and cDNA synthesis.

Total cellular RNA was isolated from control lymph nodes, and lymph nodes from breast cancer subjects using a guanidinum thiocyanate-phenol-chloroform solution (RNA STAT-60™; TEL-TEST, Friendswood, Tex.). Lymph node specimens were removed from −70° C. storage and weighed as quickly as possible without allowing the tissue to thaw. SLN were processed separately from ALN. A maximum of three ALN were pooled together into one sample while SLN were analyzed individually. If a subject had only one small SLN it was combined with the ALN. Tissue ($\leq 0.15$ g) was then homogenized in 1 ml of RNA STAT-60™ using a model 395 type 5 polytron (Dremel, Racine, Wis.). Total RNA was isolated as per the manufacturer's instructions with the exception that 1 µl of a 50 mg/ml solution of glycogen (Sigma, St. Louis, Mo.) was added to the aqueous phase prior to addition of isopropanol. Finally, an RNA pellet was dissolved in 50 µl of 1×RNA secure buffer (Ambion, Austin, Tex.). RNA was quantified by spectrophotometry at 260 nm. cDNA was made from 5 μg of total RNA using 200 U of M-MLV reverse transcriptase (Promega, Madison, Wis.) and 0.5 μg Oligo (dT)$_{12-16}$ in a reaction volume of 20 μl (10 min at 70° C., 50 min at 42° C., 15 min at 70° C.).

Real-time RT-PCR.

Real-time RT-PCR primers have been previously reported [10, 59]:

```
mglo:
F 5'-GCCGTGTGAACCATGTGACTTT,    (SEQ ID NO:15)
R 5'-CCAAATGCGGCATCTTCAAA;      (SEQ ID NO:16)

PDEF:
F 5'-AGTGCTCAAGGACATCGAGACG,    (SEQ ID NO:17)
R 5'-AGCCACTTCTGCACATTGCTG;     (SEQ ID NO:18)

mam:
F 5'-CGGATGAAACTCTGAGCAATGT,    (SEQ ID NO:1)
R 5'-CTGCAGTTCTGTGAGCCAAAG;     (SEQ ID NO:2)

CK19:
F 5'-CATGAAAGCTGCCTTGGAAGA,     (SEQ ID NO:13)
R 5'-TGATTCTGCCGCTCACTATCAG;    (SEQ ID NO:14)

muc1:
F 5'-ACCATCCTATGAGCGAGTACC,     (SEQ ID NO:9)
R 5'-GCCACCATTACCTGCAGAAAC;     (SEQ ID NO:10)

PIP:
F 5'-GCCAACAAAGCTCAGGACAAC,     (SEQ ID NO:5)
R 5'-GCAGTGACTTCGTCATTTGGAC;    (SEQ ID NO:6)

mamB:
F 5'-AGCAGTGTTTCCTCAACCAGTC,    (SEQ ID NO:19)
R 5'-TCTGAGCCAAACGCCTTG.        (SEQ ID NO:20)
```

Real-time RT-PCR analyses were performed on a PE Biosystems Gene Amp® 5700 Sequence Detection System (Foster City, Calif.). All reaction components were purchased from PE Biosystems. The standard reaction volume was 10 μl and contained 1×SYBR Green PCR Buffer; 3.5 mM MgCl$_2$; 0.2 mM each of dATP, dCTP, and dGTP; 0.4 mM of dUTP; 0.25 U AmpliTaq Gold®; 0.1 U AmpErase® UNG enzyme; 0.7 μl cDNA template; and 0.25 mM of both forward and reverse primer. The initial step of PCR was 2 min at 50° C. for AmpErase® UNG activation, followed by a 10-min hold at 95° C. Cycles (n=40) consisted of a 15 sec denaturation step at 95° C., followed by a 1 min annealing/extension step at 60° C. The final step was a 60° C. incubation for 1 min. All reactions were performed in triplicate. The threshold for cycle of threshold ($C_t$) analysis was set at 0.5 relative fluorescence units.

Primary data analysis.

Real-time RT-PCR data were quantified in terms of cycle threshold ($C_t$) values. Ct values are inversely related to the amount of starting template; high $C_t$ values correlate with low levels of gene expression, whereas low $C_t$ values correlate with high levels of gene expression. Results were normalized to an internal control reference gene, β2-microglobin, by subtracting the mean $C_t$ value of β2-microglobin from the mean $C_t$ value of each respective gene ($\Delta C_t$ value). Samples for which $C_t$ values for β$_2$-microglobin were equal or higher than 22 were considered to contain inadequate RNA and were excluded from the analysis. In order to define baseline levels of gene expression and to define thresholds for marker positivity, 51 cervical lymph nodes from patients with no evidence of malignancy were analyzed. The size of this control group was based on 95% confidence interval data obtained from Geigy Scientific Tables as reported by Henderson [60]. Threshold values for each individual marker were set at three standard deviations below the mean $\Delta C_t$ value in the normal control group. A subject was considered to be positive for the molecular analysis if at least one marker in the panel was below the defined threshold. Data from real-time RT-PCR analyses were compiled in a Microsoft Access database and submitted to The Clinical Innovation Group (TCIG) at the Medical University of South Carolina for statistical analyses.

Receiver operating characteristic (ROC) curve analysis.

Data from control normal lymph nodes and ALN from subjects with pathology-positive ALN were analyzed using MATLAB 6.5® (R13) programming environment, MathWorks Inc.

Artificial neural network analysis.

The ANN analysis was developed by following the guidelines stipulated in [61]. Those guidelines consist of using bootstrapped cross-validation for automatic identification of ANN models, including both regression early stopping and optimal topology selection, while avoiding model over-fitting.

Statistical analysis.

Simple descriptive summary statistics (means ±standard deviations for continuous variables and proportions for categorical variables) were obtained to describe the demographic and clinical characteristics of the study sample. Degree of agreement between pathological and molecular results was calculated as a Kappa statistic. Logistic regression analyses were performed using SAS Version 8.0 Software (SAS Institute Inc., SAS Campus Drive, Cary, N.C.) for the analysis of pathological and molecular outcome adjusting for pre-defined baseline covariates that have been associated with pathological outcome in prior studies. Pre-defined baseline covariates were tumor size, histological grade, estrogen receptor status, progesterone receptor status, her2neu status, and St. Gallen risk category (minimal/low risk: tumor size ≦1 cm, positive ER and/or PR status, grade I and age ≧35; intermediate risk: tumor size >1-2 cm, positive ER and/or PR status, and grade I; and high risk: tumor size >2 cm, negative ER and/or PR status, grade II-III or age <35) [62]. Statistical significance was defined as p-values <0.05.

Results

Demographic and clinical characteristics.

A total of 489 subjects with breast cancer from 14 medical centers were included in this analysis. Demographic and clinical characteristics of the subjects are listed in Table 6. Sixty one (11%) subjects who initially consented were excluded from the final analysis due to one or more of the following reasons: subject withdrawal of consent (n=6), subject ineligibility (n=13), standard histopathology unavailable (n=18), specimens lost or thawed during shipment (n=17), or uninterpretable real-time RT-PCR results (n=7). Reasons for subject ineligibility included invasive cancer or lymphoma found in the contralateral breast, previous diagnosis or treatment of cancer within the exclusionary timeframe, diagnosis of ALN metastases prior to subject registration, and final diagnosis of DCIS without invasive breast cancer.

Precise quantitation of baseline gene expression levels in control lymph nodes defines marker thresholds for real-time RT-PCR analyses.

Figure 3:
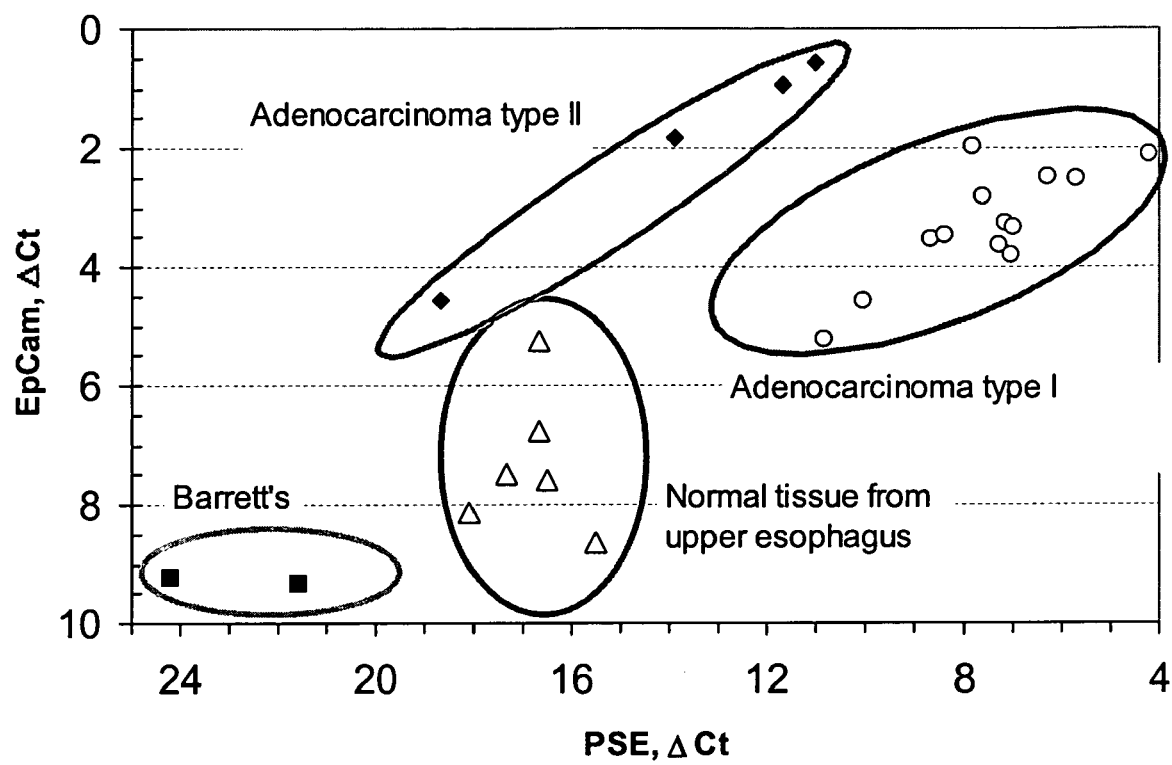
FIG. 3 shows real time RT-PCR studies were performed on 17 adenocarcinomas of the esophagus, 6 normal tissues from the upper esophagus (open triangles), and 2 Barrett's esophagus samples (obtained from the same patient (filled squares)) using a 7-gene marker panel. The results of two of the genes are shown above and reveal a clustering of the samples according to histologic tissue type. Two distinct clusters of adenocarcinomas can also be observed, which are arbitrarily designated "type I" (open circles) and "type II" (filled diamonds).
Figure 4:
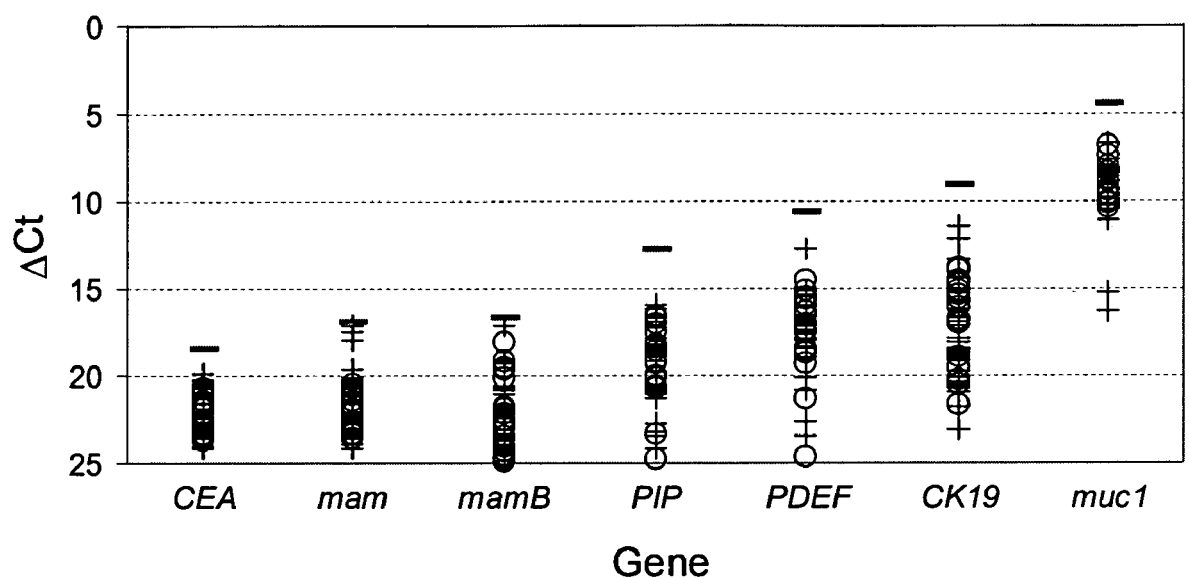
FIG. 4 shows expression of cancer-associated genes in normal control lymph nodes. Real-Time RT-PCR analysis of lymph nodes from 51 negative control patients (32 males (+), 19 females (O)) was performed as described in Materials and Methods using primer pairs for the indicated genes. Ct values for each gene were determined from triplicate reactions. ΔCt values were obtained by subtracting the mean Ct value of $\beta_2$-microglobin from the mean Ct value of each respective gene. Horizontal lines indicate ΔCt threshold values (3 standard deviations below the mean). Mean ΔCt and ΔCt threshold for each gene are as follows: CEA 22.23, 18.45; mam 21.5, 16.9; mamB 22.49, 16.63; PIP 19.18, 12.68; PDEF 17.64, 10.61; CK19 17.25, 9.04; muc19.35, 4.43.
Figure 5:
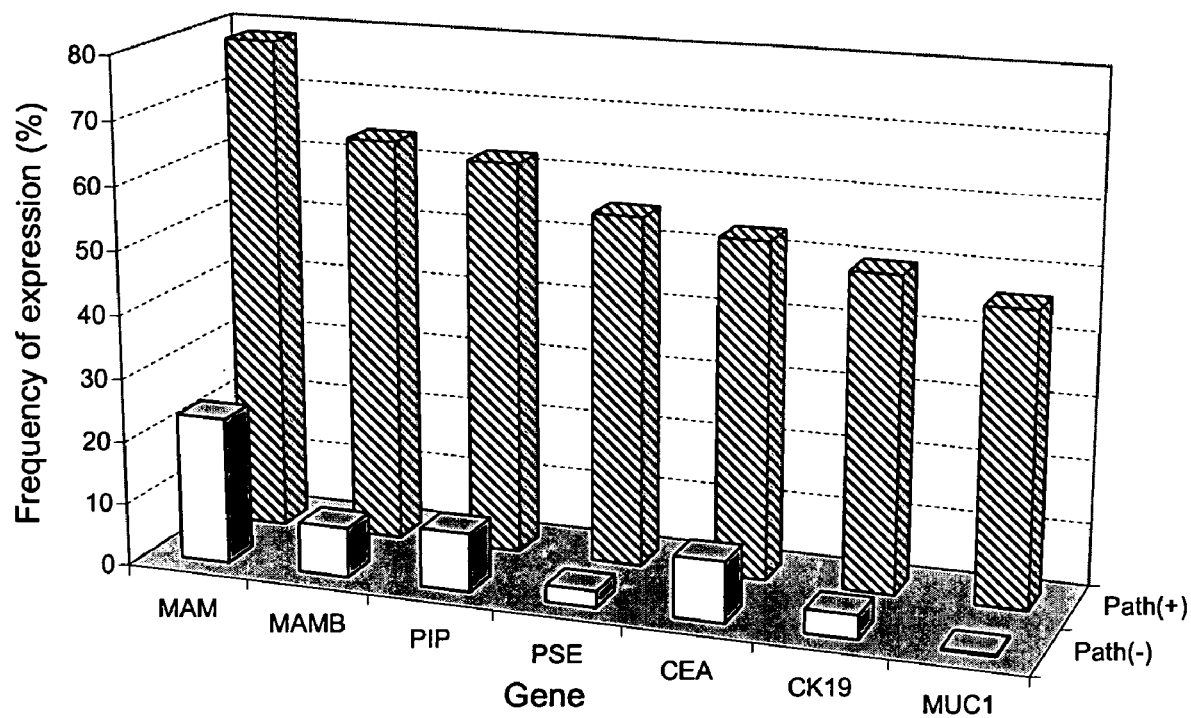
FIG. 5 shows frequency of gene expression in breast cancer subjects with pathology-positive (Path(+)) and pathology-negative (Path(−)) ALN. Real-time RT-PCR analysis of ALN from 145 subjects with pathology-positive ALN and 344 subjects with pathology-negative ALN was performed as described in the Materials and Methods using primer pairs for the indicated genes. Marker positivity was determined based on ΔCt threshold values. Y-axis shows the percent of subjects positive for each respective gene.

An ideal molecular diagnostic marker would have no detectable expression in normal tissues and would have substantial expression in cancer cells. Nevertheless, the majority of known breast cancer-associated genes have some background expression in normal lymph nodes [10, 59]. For this study seven breast cancer-associated genes (mam, mamB, PIP, CK19, muc1, PDEF, and CEA) that are known to be overexpressed in metastatic breast cancer compared to control lymph nodes were selected [10, 59]. Baseline gene expression was precisely quantitated in 51 control lymph nodes by real-time RT-PCR. To obtain maximum specificity, threshold values for marker positivity were set at three standard deviations beyond the mean $\Delta C_t$ value for each gene (FIG. 4). At the defined threshold values, positivity was not observed for any marker in the normal control samples. The frequency of marker overexpression for the individual markers is shown in FIG. 5.

Receiver operating curve analysis defines the diagnostic accuracy of individual markers for the detection of metastatic breast cancer.

Figure 6:
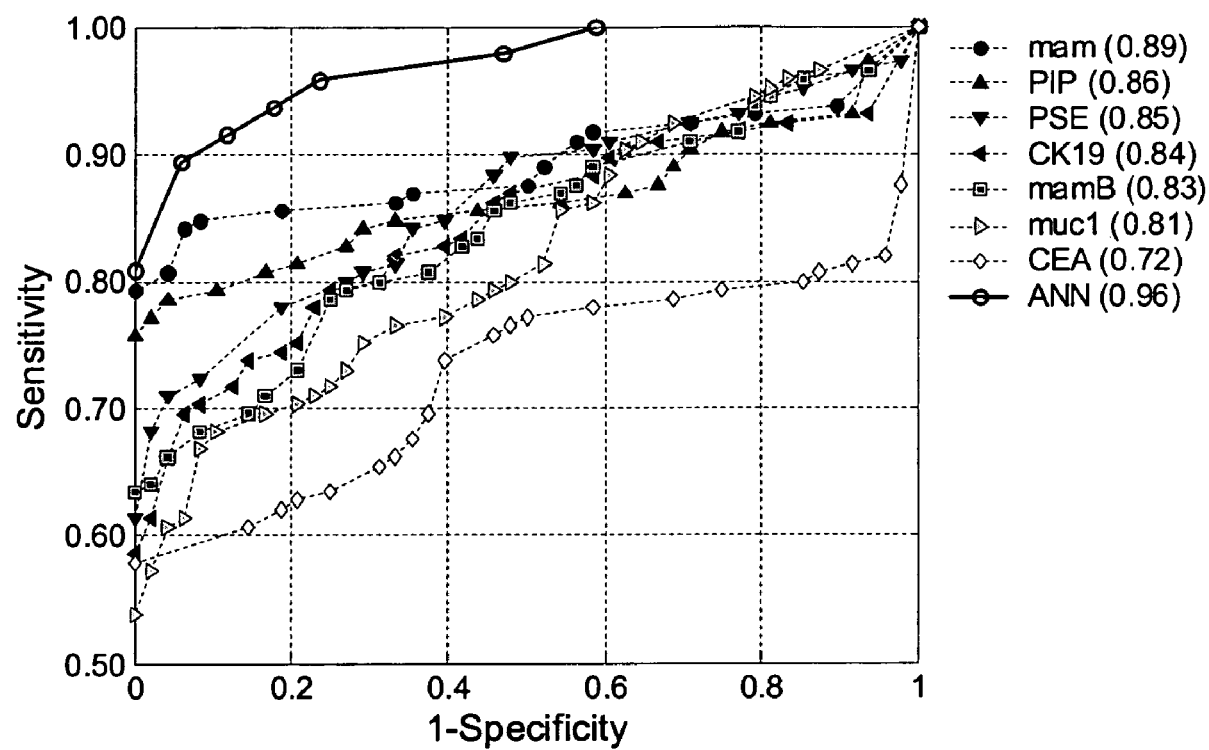
FIG. 6 shows receiver operating characteristic (ROC) curve analysis of the seven individual molecular markers. ROC curve analysis was performed using data from 145 subjects with pathology-positive ALN, and 51 control subjects. The analysis was performed in MATLAB 6.5® (R13)

To rigorously define the value of the real-time RT-PCR analysis for the detection of metastatic breast cancer, a receiver operator characteristic (ROC) curve analysis was performed using MATLAB 6.5® (R13) programming environment. ROC curve analysis is the most commonly used method for assessing the accuracy of diagnostic tests [60]. ROC curve analysis is based on a plot of sensitivity as a function of 1-specificity. The area under the ROC curve (W) is a measure of diagnostic accuracy such that values between 0.5 and 0.7 indicate low accuracy, values between 0.7 to 0.9 indicate moderate accuracy and values greater than 0.9 indicate high accuracy [63]. With respect to diagnosis of metastatic breast cancer, mam exhibited the highest level of accuracy (W=0.89); values for the remaining genes are listed in FIG. 6. The results of this ROC curve analysis closely parallel the results obtained in [10].

Multi-marker analysis improves the sensitivity of molecular detection of breast cancer metastases.

For the real-time RT-PCR analyses in this study a panel of seven genes was used. In order to determine the value of multi-marker analysis for the detection of metastatic and micrometastatic breast cancer, the frequency of gene overexpression for various marker combinations was determined (FIG. 7). In patients with pathology-positive ALN, mam was the most sensitive marker, and was overexpressed in 114 subjects, or 90.5% of the 126 subjects who were positive by molecular analyses. This result is consistent with previous studies demonstrating that mam has the highest diagnostic accuracy for the detection of metastatic breast cancer [10, 64]. Of the patients in this subgroup (pathology-positive ALN, positive by molecular analyses) who did not overexpress mam, CEA was the next most valuable marker; the combination of mam and/or CEA (i.e., a two-gene marker panel) was positive in 123 of 126 (97.6%) subjects (FIG. 4). Of the patients in this subgroup who did not express mam or CEA, PIP was the next most valuable marker; the combination of mam and/or CEA and/or PIP (i.e., a three-gene marker panel) detected gene overexpression in 125 of 126 (99.2%) subjects.

To determine the value of multi-marker analysis for the detection of micrometastatic disease in subjects with pathology-negative ALN, the frequency of gene overexpression for various marker combinations was determined as described above (FIG. 7). Similar to the results obtained in subjects with pathology-positive ALN, of all the possible three-gene marker combinations, the one consisting of mam, CEA and PIP yielded the highest apparent sensitivity for micrometastatic disease detection (FIG. 7). However, in contrast to a detection rate of 99.2% observed in patients with pathology-positive ALN, the detection rate for this three marker panel was reduced to 93.8% in patients with pathology-negative ALN. These data suggest that multi-marker analysis is more important for the detection of micrometastatic disease than metastatic disease.

In order to further define the value of using a multi-marker analysis, sensitivity and specificity using artificial neural networks (ANN) were modeled. For this multiparametric ANN model, a validation dataset was used comprising one-third of the total data excluded from ANN training (see Materials and Methods for details on the bootstrapping procedure). ROC curve analysis was then performed. The results of this ANN (AUC 0.96) significantly outperformed the best individual molecular marker (mam, AUC 0.89), as well as a conventional multi-logistic regression approach (AUC 0.91) for the validation set. These data provide statistical confirmation of the value of the multi-marker analysis.

Specific subgroup analyses reveal that the distribution of molecular results parallels the distribution of standard histopathology results.

Of the 489 subjects enrolled in the MIMS Trial, 145 (30%) had one or more pathology-positive ALN and 344 (70%) had pathology-negative ALN based on standard histopathology. The real-time RT-PCR analyses of these ALN revealed a positive marker signal in 126/145 (87%) of subjects with pathology-positive ALN, and in 112/344 (33%) subjects with pathology-negative ALN. To determine whether the results of the molecular analyses were correlated with traditional prognostic indicators, three specific subgroup analyses were performed: 1) the distribution of positive standard histopathology in ALN of all subjects (n=489), 2) the distribution of positive molecular analyses in ALN of all subjects (n=489), and 3) the distribution of positive molecular analyses in ALN of subjects with pathology-negative ALN (n=344) (Table 7). In all three groups, the distribution of positive results (standard histopathology or real-time RT-PCR) increased with tumor size, clinical stage, histological grade (grade I vs. grade II & III), Her2neu status, and St. Gallen risk category (Table 2). These data show that the distribution of real-time RT-PCR results is associated with traditional indicators of prognosis.

Logistic regression confirms that molecular analyses are associated with traditional indicators of prognosis.

To determine the statistical significance of the apparent association between molecular analyses and traditional risk factors, individual logistic regression analyses were performed using standard histopathology or molecular status of ALN (positive vs. negative) as the dependent variable and with the following clinical parameters as independent variables: tumor size, histological grade, ER status, PR status, Her2neu status, and St. Gallen risk category (Table8). Table 8A presents the results of the logistic regression analyses for the distribution of positive standard histopathology in ALN of all patients (n=489). As expected, standard histopathology of ALN was significantly associated with tumor size (>1 cm vs $\leq$1 cm; p<0.0001, OR=5.937, 95% CI (3.159, 11.159)), histologic grade (II-III vs I; p=0.0018, OR=2.162, 95% CI (1.331, 3.511)), and St. Gallen risk category (high vs low/intermediate; p=0.0028, OR=2.316, 95% CI (1.335, 4.018)). Table 8B presents the results of the logistic regression analyses for the distribution of positive molecular analyses in ALN of all patients (n=489). Significant associations were observed with tumor size (p<0.0001, OR=2.608, 95% CI (1.711, 3.975)), histologic grade (p=0.0003, OR=2.163, 95% CI (1.428, 3.275)), and St. Gallen risk category (p=0.0009, OR=2.155, 95% CI (1.369, 3.393)). Table 8C presents the results of the logistic regression analyses for the distribution of positive molecular analyses in ALN of subjects with pathology-negative ALN (n=344). Even though positive molecular analyses clearly increased with tumor size, this did not reach statistical significance (p=0.0889). However, molecular analyses were significantly associated with histologic grade (p<0.0255,OR=1.799, 95% CI (1.075, 3.012)) and St. Gallen risk category (p<0.0220, OR=1.946, 95% CI (1.101, 3.441)). The collective findings from these logistic regression analyses confirm that the real-time RT-PCR analyses are significantly correlated with clinical parameters that predict a poor prognosis in the entire subject cohort (n=489) and in the subset of subjects, patients with pathology-negative ALN (n=344). This rigorous statistical analysis strongly suggests that the molecular markers described in this study serve as valid surrogates for the detection of metastatic and micrometastatic breast cancer.

To determine the clinical relevance of molecular detection of metastatic and micrometastatic breast cancer, a multi-institutional prospective cohort study (the MIMS Trial) using a panel of molecular markers with moderate to high diagnostic accuracy for the detection of breast cancer metastases was initiated [10, 59]. The MIMS Trial provides data that advance the field of breast cancer molecular diagnostics for several reasons. First, analyses were performed using quantitative real-time RT-PCR and a multi-marker gene panel. Second, threshold levels for marker positivity were based on quantitative analyses of a significant number of normal control lymph nodes (n=51). Third, the study was prospectively designed, all real-time RT-PCR assays were performed in a blinded manner, and the results were analyzed by an independent statistical group. Finally, the number of subjects analyzed in the study (n=489) provides the statistical power required to define the clinical relevance of molecular detection of breast cancer micrometastases.

Multi-marker real-time RT-PCR analyses of ALN from 489 breast cancer subjects have been completed. The results indicate that 33% of subjects with pathology-negative ALN have a positive marker signal in their lymph nodes by real-time RT-PCR. The primary hypothesis of the MIMS Trial is that in this subgroup of patients with pathology-negative ALN the overexpression of a positive marker signal will be associated with poor clinical outcome (defined as the proportion of subjects having disease relapse within five years of diagnosis). In support of this hypothesis, Table 7 demonstrates that the rate of marker positivity increased with tumor size, histological grade (grade I vs. grade II & III), Her2neu expression, and St. Gallen risk category (Table 7). Even though the associations between marker positivity, tumor size and Her2neu status did not reach statistical significance, the results of logistic regression analyses confirm that the associations between marker positivity, histological grade, and St. Gallen risk category are statistically significant. These data provide evidence that marker positivity is associated with clinical parameters that predict poor prognosis, a finding that strongly supports the molecular approach to micrometastatic breast cancer detection.

A major limitation of conventional RT-PCR is the inability to precisely quantify the amount of mRNA template, thus explaining the variable results that have been reported in the literature. Specifically, in the field of breast cancer molecular diagnostics, Noguchi et al. reported no expression of muc1 and CK19 in normal control lymph nodes, while studies by Min et al., Bostick et al. and Marchetti et al. demonstrate that these two markers are expressed in normal lymph nodes, and therefore not suitable for molecular detection of micrometastatic breast cancer [44, 47, 65, 66]. The study by Bostick et al. also showed expression of CEA in normal lymph nodes, while Min et al., Marchetti et al. and Masuda et al. failed to detect expression of CEA in normal lymph nodes [47, 65-67].

To date, only one prospective study designed to assess the value of molecular detection of micrometastatic breast cancer has been reported [68]. Sakaguchi et al. reported that 16% of patients with pathology-negative ALN had evidence of CK19 overexpression by conventional RT-PCR. However, these results were not clinically relevant; outcomes for patients who overexpressed CK19 were not significantly different from the outcomes for patients who did not overexpress this marker. In the present study overexpression of CK19 was detected in only 3.8% of the subjects with pathology-negative ALN, a value that is significantly lower than that of Sakaguchi et al,. These results suggest that Sakaguchi et al. may not have been able to differentiate between baseline CK19 expression and CK19 overexpression using conventional RT-PCR, leading to a significant number of false positive results. This limitation of conventional PCR is addressed directly in the MIMS Trial by the use of quantitative real-time RT-PCR.

In terms of the diagnostic accuracy of the individual molecular markers, the results of ROC curve analyses from the MIMS Trial are remarkably similar to ROC curve analyses published previously [10]. Mam clearly appears to be the most valuable molecular marker for the detection of metastatic breast cancer in ALN, and is overexpressed in 79% of subjects with pathology-positive ALN (or 90% of subjects with pathology-positive ALN who were marker-positive). This result is concordant with previous work where mam was overexpressed in 94% of pathology-positive lymph nodes [10]. It is also concordant with the study by Zehentner et al., in which mam was detected by real-time RT-PCR in 80% of pathology-positive ALN [64]. Studies using conventional RT-PCR have also validated the high diagnostic accuracy of mam with sensitivities ranging from 78% to 100% and specificities ranging from 86% to 100% [65, 66, 58, 69, 70]. Although the other individual markers are less sensitive than mam, ROC curve analyses confirm that they all have moderate to high accuracy for the detection of metastatic breast cancer.

The use of multi-marker gene panels for the detection of metastatic breast cancer has been proposed by many investigators [40, 10, 64, 65, 58, 71]. The results of the MIMS Trial confirm that a combination of markers significantly improves the value of the molecular assay. First, the sensitivity of the assay is significantly improved using the multi-marker panel. Second, sophisticated statistical models permit ROC curve analysis of the multi-marker assay, and the results confirm that the diagnostic accuracy is significantly increased compared to the best individual marker. However, the present study also suggests that a multi-marker gene panel is most important for the detection of micrometastatic disease (low tumor burden). The data indicate that to obtain a sensitivity of 97% in subjects with marker-positive/pathology-positive ALN, a two-marker gene panel is sufficient (mam, CEA). However, to obtain a similar level of sensitivity in subjects with marker-positive/pathology-negative ALN a four-marker gene panel is required (mam, CEA, PIP, CK19) (FIG. 7). These results suggest that in pathology-negative ALN, where the disease burden is presumed to be low, the diagnostic accuracy of the individual molecular markers is decreased, and an extended maker panel is required in order to achieve maximum detection of micrometastatic disease.

Overall, the sensitivity of multi-marker real-time RT-PCR for the detection of metastatic breast cancer was 87%. Evaluation of the 19 subjects with pathology-positive ALN who were marker-negative (false-negatives) revealed a significant potential for sampling error. In fact, 15 of the 19 patients in this group had only one pathology-positive ALN, and the median number of ALN analyzed by pathology was 12 per subject. In these 19 false-negative cases, the ALN containing metastatic breast cancer may not have been available for RT-PCR analysis. Another potential source of sampling error is the fact that the ALN specimens were divided at the time of collection, with half of the specimen sent for routine pathology and half for real-time RT-PCR. Thus, the study design raises the possibility that the portion of the ALN with metastatic breast cancer was sent for routine pathology but not real-time RT-PCR [72]. Thus, sampling error may help to explain the relatively low sensitivity reported in this study.

This MIMS Trial is the first prospective study to find a statistically significant association between molecular detection of breast cancer micrometastases and traditional predictors of poor prognosis in subjects with pathology-negative ALN. The present markers and marker combinations allow for staging of breast cancer with greater sensitivity and accuracy. This is particularly relevant for the analysis of SLN, as the overall accuracy of SLN biopsy appears to be predicated on the sensitive pathologic evaluation of the SLN. The development of the present sensitive molecular diagnostic assay for the detection of breast cancer micrometastases is expected to result in improved ability to tailor adjuvant therapies by identifying high-risk patients who would most likely benefit from aggressive systemic therapy.

TABLE 6

Patient demographic and clinicopathologic characteristics.

| Characteristic | N = 489 |
|---|---|
| Race: | |
| Caucasian | 421 (86.09%) |
| Black | 61 (12.47%) |
| Asian | 2 (0.41%) |
| Hispanic | 2 (0.41%) |
| Native American | 1 (0.20%) |
| Other | 2 (0.41%) |
| Family history: | |
| Yes | 77 (15.75%) |
| No | 412 (84.25%) |
| Age: | |
| Mean (StDev) | 56.8 (11.39) |
| Range | (26, 89) |
| <40 | 33 (6.75%) |
| 40-44 | 47 (9.61%) |
| 45-49 | 64 (13.09%) |
| >=50 | 345 (70.55%) |
| Primary Tumor: | |
| T1 | 334 (68.30%) |
| T2 | 145 (29.65%) |
| T3 | 10 (2.05%) |
| Nodal Metastases: | |
| $N_0$ | 344 (70.35%) |
| $N_1$ | 145 (29.65%) |
| Clinical Stage: | |
| I | 267 (54.60%) |
| IIA | 138 (28.22%) |
| IIB | 69 (14.11%) |
| IIIA | 11 (2.25%) |
| IIIB | 2 (0.41%) |
| IV | 2 (0.41%) |
| Histologic Grade: | |
| I | 133 (27.20%) |
| II | 195 (39.88%) |
| III | 136 (27.81%) |
| ER Status: | |
| ER-neg | 107 (21.88%) |
| ER-pos | 360 (73.62%) |

TABLE 6-continued

Patient demographic and clinicopathologic characteristics.

| Characteristic | N = 489 |
|---|---|
| PR Status: | |
| PR-neg | 156 (31.90%) |
| PR-pos | 284 (58.08%) |
| Her2neu Status: | |
| Her2neu-neg | 218 (44.58%) |
| Her2neu-pos | 89 (18.20%) |
| Histologic Type: | |
| Infilatrating Ductal | 394 (80.57%) |
| Infiltrating Lobular | 44 (9.00%) |
| Medullary Carcinoma | 1 (0.21%) |
| Tubular Carcinoma | 12 (2.45%) |
| Mucoid Carcinoma | 2 (0.41%) |
| Papillary Carcinoma | 5 (1.02%) |
| Other | 30 (6.14%) |
| Risk Category: | |
| LowRisk | 53 (10.84%) |
| Intermediate Risk | 50 (10.23%) |
| High Risk | 386 (78.94%) |

TABLE 7

Pathology and PCR status of ALN in all patients (n = 489) and pathology-negative patients (n = 344).

| | All patients (n = 489) | | Path-neg patients (n = 344) Path- |
|---|---|---|---|
| Characteristic | Path-pos | PCR-pos | neg/PCR-pos |
| Primary Tumor: | | | |
| T1 | 66/334 (20%) | 139/334 (42%) | 83/268 (31%) |
| T2 | 71/145 (49%) | 91/145 (63%) | 28/74 (38%) |
| T3 | 8/10 (80%) | 8/10 (80%) | 1/2 (50%) |
| Clinical Stage: | | | |
| I | *** | 83/267 (31%) | 83/267 (31%) |
| IIA | 63/138 (46%) | 81/138 (59%) | 28/75 (37%) |
| IIB | 67/69 (97%) | 61/69 (88%) | 1/2 (50%) |
| IIIA + IIIB + IV | 15/15 (100%) | 13/15 (87%) | *** |
| Histologic Grade: | | | |
| I | 26/133 (20%) | 48/133 (36%) | 27/107 (25%) |
| II | 64/195 (33%) | 109/195 (56%) | 54/131 (41%) |
| III | 50/136 (37%) | 73/136 (54%) | 28/86 (33%) |
| ER Status: | | | |
| ER-negative | 29/107 (27%) | 53/107 (50%) | 29/78 (37%) |
| ER-positive | 108/360 (30%) | 171/360 (48%) | 77/252 (31%) |
| PR Status: | | | |
| PR-negative | 45/156 (29%) | 76/156 (49%) | 37/111 (33%) |
| PR-positive | 80/284 (28%) | 133/284 (47%) | 63/204 (31%) |
| Her2neu Status: | | | |
| Her2neu-negative | 57/218 (26%) | 90/218 (41%) | 42/161 (26%) |
| Her2neu-positive | 28/89 (32%) | 47/89 (53%) | 22/61 (36%) |
| Risk Categories: | | | |
| Low Risk | 5/53 (9%) | 14/53 (26%) | 10/48 (21%) |
| Intermediate | 13/50 (26%) | 21/50 (42%) | 9/37 (24%) |

TABLE 7-continued

Pathology and PCR status of ALN in all patients (n = 489) and pathology-negative patients (n = 344).

| Characteristic | All patients (n = 489) | | Path-neg patients (n = 344) Path-neg/PCR-pos |
|---|---|---|---|
| | Path-pos | PCR-pos | |
| Risk | | | |
| High Risk | 127/386 (33%) | 203/386 (53%) | 93/259 (36%) |

TABLE 8A

Logistic Regression Models Modeling Probability of Positive Pathology in N = 489 Subjects Relative to Clinical Variables

| Variable | $\chi^2$ p-value | Odds Ratio | 95% Confidence Interval |
|---|---|---|---|
| Tumor Size > 1 cm (vs <= 1 cm) | <0.0001 | 5.937 | 3.159, 11.159 |
| Histological Grade II-III (vs I) | 0.0018 | 2.162 | 1.331, 3.511 |
| ER Status negative (vs positive) | 0.5635 | 0.868 | 0.536, 1.405 |
| PR Status negative (vs positive) | 0.8800 | 1.034 | 0.671, 1.593 |
| Her2neu Status positive (vs negative) | 0.3458 | 1.297 | 0.756, 2.224 |
| Risk high (vs low/intermediate) | 0.0028 | 2.316 | 1.335, 4.018 |

TABLE 8B

Logistic Regression Models Modeling Probability of Positive Molecular Analysis in N = 489 Subjects Relative to Clinical Variable

| Variable | $\chi^2$ p-value | Odds Ratio | 95% Confidence Interval |
|---|---|---|---|
| Tumor Size > 1 cm (vs <= 1 cm) | <0.0001 | 2.608 | 1.711, 3.975 |
| Histological Grade II-III (vs I) | 0.0003 | 2.163 | 1.428, 3.275 |
| ER Status negative (vs positive) | 0.7116 | 1.085 | 0.704, 1.671 |
| PR Status negative (vs positive) | 0.7045 | 1.079 | 0.730, 1.595 |
| Her2neu Status positive (vs negative) | 0.0662 | 1.592 | 0.969, 2.613 |
| Risk high (vs low/intermediate) | 0.0009 | 2.155 | 1.369, 3.393 |

TABLE 8C

Logistic Regression Models Modeling Probability of Positive Molecular Analysis in N = 344 Subjects with Pathology-Negative ALN Relative to Clinical Variables

| Variable | $\chi^2$ p-value | Odds Ratio | 95% Confidence Interval |
|---|---|---|---|
| Tumor Size > 1 cm (vs <= 1 cm) | 0.0889 | 1.528 | 0.938, 2.489 |
| Histological Grade II-III (vs I) | 0.0255 | 1.799 | 1.075, 3.012 |
| ER Status negative (vs positive) | 0.2745 | 1.345 | 0.790, 2.289 |
| PR Status negative (vs positive) | 0.6554 | 1.119 | 0.683, 1.834 |
| Her2neu Status positive (vs negative) | 0.1445 | 1.598 | 0.851, 3.001 |
| Risk high (vs low/intermediate) | 0.0220 | 1.946 | 1.101, 3.441 |

Example 5

Application of Population-Based Statistical Theory to a Multi-Institutional Prospective Cohort Study Indicates that Mammaglobin is the Most Reliable Marker for Detection of Micrometastatic Breast Cancer The objective of this study was to determine whether overexpression of cancer-associated genes in axillary lymph nodes of breast cancer patients correlates with clinical outcome (5 year follow-up).

Although a number of genes have been identified as surrogate markers of metastatic breast cancer, it is not known which (if any) genes can reliably detect occult disease. For a molecular marker to be considered as a valid surrogate of occult disease, its rate of disease detection in tissues suspected to contain minimal disease must be 1) higher compared to other candidate markers, and 2) proportional to its Relative Level of Overexpression (RLO) in metastatic tissue compared to non-metastatic tissue. To determine what breast cancer markers are reliable surrogates of occult disease in axillary lymph nodes (ALNs), marker distribution frequency data were generated and then mean expression levels in metastatic (H&E positive; n=145 ALNs) and non-metastatic (H&E negative; n=344 ALNs) populations of seven genes associated with metastatic breast cancer were determined. This population-based statistical approach, which revealed unambiguous bimodal distributions of all genes expressed in H&E positive ALNs, resulted in the following calculated gene RLO values: $2.6 \times 10^2$ (muc1), $7.2 \times 10^2$ (CK19), $2.6 \times 10^3$ (CEA), $3.3 \times 10^3$ (PSE), $2.1 \times 10^4$ (mamB), $1.1 \times 10^5$ (PIP), and $6.2 \times 10^6$ (mam). The correlation between log [RLO] values and respective positivity rates for detection of occult disease in H&E negative patients was very high ($R^2$=0.86, p<0.01), thus providing statistical evidence that mam is the most reliable surrogate of breast cancer occult metastatic disease. The quantitative nature of this analysis leads to the conclusion that the sensitivity of cancer cell detection by hematoxylin and eosin (H&E) staining in ALNs (estimated at one cancer cell per 400 normal lymph node cells) is comparable to detection by muc1.

In this study, axillary lymph nodes from 489 early stage breast cancer patients from twelve clinical centers were examined. Of the 489 patients, 344 were H&E positive, and 145 were H&E negative. After RNA was isolated from the lymph nodes, real-time PCR was performed on mam, mamB, CK19, CEA, muc1, PSE, and PIP as described in [10, 59]. After this procedure, threshold values were assigned based on control negatives to determine marker positivity.

Preliminary marker analysis showed that apparent detection of micrometastatic disease correlates poorly with ROC area under the curve measurements (FIGS. 8A and 8B).

Population-based hypothesis: The rate of micrometastatic disease detection of any reliable surrogate marker must be proportional to its Relative Level of Overexpression (RLO) in metastatic tissue compared to non-metastatic tissue. See FIGS. 9A and 9B.

Marker validation, part 1: Generation of marker distribution (density) frequency data from H&E positive and H&E negative patients using MATLAB® software is shown in FIGS. 10A-10G. Frequency distributions of the indicated genes were generated using MATLAB 6.5® software (R13, MathWorks Inc., Natick Mass.) for H&E positive (n=145) and H&E negative (n=344) samples.

Frequency (Density) Distributions of Molecular Markers Expressed in Axillary Nodes of Breast Cancer Patients Marker validation, part 2: Data analysis reveals that detection of occult metastatic disease in H&E negative patients correlates with relative level of marker overexpression as shown in Table 9.

TABLE 9

Population-based statistical analysis of real-time RT-PCR data generated from breast cancer patients.

| Gene | ΔCt of Peak 1[1] | ΔCt of Peak 2[2] | ΔΔCt[3] | AE[4] | RLO[5] | Log [RLO] |
|---|---|---|---|---|---|---|
| mam | 0.02 | 23.25 | 23.23 | 0.96 | 6.16E+06 | 6.79 |
| PIP | 2.09 | 20.99 | 16.77 | 1.00 | 1.12E+05 | 5.05 |
| mamB | 9.90 | 24.33 | 14.43 | 0.99 | 2.05E+04 | 4.31 |
| CEA | 12.09 | 23.98 | 11.89 | 0.94 | 2.64E+03 | 3.42 |
| PSE | 4.57 | 16.27 | 11.70 | 1.00 | 3.32E+03 | 3.52 |
| CK19 | 1.94 | 14.92 | 12.98 | 0.66 | 7.21E+02 | 2.86 |
| muc1 | 0.85 | 8.88 | 8.03 | 1.00 | 2.62E+02 | 2.42 |

[1]Corresponds to high expressing peak observed in H&E(+) population.
[2]Corresponds to low expressing peak observed in H&E(−) population.
[3]Difference between Peak2 and Peak1.
[4]Amplification Efficiency of respective gene.
[5]Determined from the equation $(1 + AE)^{\Delta\Delta Ct}$ Marker positivity rates in H&E negative patients correlates well with log [RLO] values. RLO values for each gene were obtained from Table 9 and are plotted as a function of marker positivity rates in H&E negative patients (n=344). Correlation coefficient was obtained using Microsoft Excel® software. P value was obtained using Fisher's exact test. See FIG. 11.

The results described in this Example provide statistical evidence that the most reliable molecular markers for detection of occult metastatic breast cancer are mam>PIP>mamB. Further, the positivity rate for detection of occult metastatic disease was highest for mam (23.8%), indicating that this gene was the most sensitive. Based on linear regression analysis, the estimated false positive rate for mam was only 1.2%, indicating that this marker was also the most specific. Based on the y-intercept value of the regression line, it was concluded that for a given marker to have any value for detection of micrometastatic disease, it must be able to detect one metastatic cancer cell in a background of $10^{2.6}$ (or 400) normal lymph node cells, assumed to be the approximate level of cancer cell detection by H&E staining.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

References

1. Mountain C F, Dresler C M 1997 Regional lymph node classification for lung cancer staging. Chest 111(6):1718-23.
2. Kurusu Y, Yamashita J, Ogawa M 1999 Detection of circulating tumor cells by reverse transcriptase-polymerase chain reaction in patients with resectable non-small-cell lung cancer. Surgery 126(5):820-6.
3. Salerno C T, Frizelle S, Niehans G A, Ho S B, Jakkula M, Kratzke R A, Maddaus M A 1998 Detection of occult micrometastases in non-small cell lung carcinoma by reverse transcriptase-polymerase chain reaction. Chest 113(6):1526-32.
4. Peck K, Sher Y P, Shih J Y, Roffler S R, Wu C W, Yang P C 1998 Detection and quantitation of circulating cancer cells in the peripheral blood of lung cancer patients. *Cancer Res* 58(13):2761-5.
5. Wallace B, Silvestri G, Sahai A, Hawes R, Hoffman B, Durkalski V, Hennesey W, Reed C 2001 Endoscopic ultrasound-guided fine needle aspiration for staging patients with carcinoma of the lung. Ann Thor Sur 72:1861-1867.
6. Perez M S, Walker L E 1989 Isolation and characterization of a cDNA encoding the KS1/4 epithelial carcinoma marker. *J. Immunol.* 142:3662-3667.
7. Iwao K, Watanabe T, Fujiwara Y, Takami K, Kodama K, Higashiyama M, Yokouchi H, Ozaki K, Monden M, Tanigami A 2001 Isolation of a novel human lung-specific gene, LUNX, a potential molecular marker for detection of micrometastasis in non-small-cell lung cancer. *Int J Cancer* 91(4):433-7.
8. Bingle C D, Bingle L 2000 Characterisation of the human plunc gene, a gene product with an upper airways and nasopharyngeal restricted expression pattern. *Biochim Biophys Acta* 1493(3):363-7.
9. Sung Y K, Moon C, Yoo J Y, Pearse D, Pevsner J, Ronnett G V 2002 Plunc, a member of the secretory gland protein family, is up-regulated in nasal respiratory epithelium after olfactory bulbectomy. *J Biol Chem* 277(15):12762-9.
10. Mitas M, Mikhitarian K, Walters C, Baron P L, Elliott B M, Brothers T E, Robison J G, Metcalf J S, Palesch Y Y, Zhang Z, Gillanders W E, Cole D J 2001 Quantitative real-time RT-PCR detection of breast cancer micrometastasis using a multigene marker panel. *Int J Cancer* 93(2):162-71.
11. Bieche I, Onody P, Laurendeau I, Olivi M, Vidaud D, Lidereau R, Vidaud M 1999 Real-time reverse transcription-PCR assay for future management of ERBB2-based clinical applications. *Clin Chem* 45(8 Pt 1): 1148-56.
12. Ririe K M, Rasmussen R P, Wittwer C T 1997 Product differentiation by analysis of DNA melting curves during the polymerase chain reaction. *Anal. Biochem.* 245:154-160.
13. Mitas, M., Cole, D. J., Hoover, L., Fraig, M. M., Mikhitarian, K., Block, M. I., Hoffman, B. J., Hawes, R. H., Gillanders, W. E. and Wallace, M. B. (2003) Real-Time RT-PCR Detects KS1/4 mRNA in Mediastinal Lymph Nodes from Patients with Non-Small Cell Lung Cancer. *Clin. Chem.*, 49, 312-5.
14. Alberti, S., Nutini, M. and Herzenberg, L. (1994) DNA □ytotoxicit prevents the amplification of TROP1, a tumor-associated cell surface antigen gene. *Proc Natl Acad Sci USA*, 91, 5833-7.

15. Robinson, R. and Royston, D. (1993) Comparison of monoclonal antibodies AUA1 and BER EP4 with anti-CEA for detecting carcinoma cells in serous effusions and distinguishing them from mesothelial cells. *Cytopathology*, 4, 267-71.
16. Bergsagel, P., Victor-Kobrin, C., Timblin, C., Trepel, J. and Kuehl, W. (1992) A murine cDNA encodes a pan-epithelial glycoprotein that is also expressed on plasma cells. *J Immunol*, 148, 590-6.
17. Ross, A., Lubeck, M., Steplewski, Z. and Koprowski, H. (1986) Identification and characterization of the CO17-1A carcinoma-associated antigen. Hybridoma 1986 Jul. ;5. 5, S21-8.
18. Strnad, J., Hamilton, A., Beavers, L., Gamboa, G., Apelgren, L., Taber, L., Sportsman, J., Bumol, T., Sharp, J. and Gadski, R. (1989) Molecular cloning and characterization of a human adenocarcinoma/epithelial cell surface antigen complementary DNA. *Cancer Res*, 49, 314-7.
19. Tomita, Y., Arakawa, F., Yamamoto, T., Kuwahara, M., Watanabe, R., Iwasaki, H., Kikuchi, M. and Kuroki, M. (2000) Molecular identification of a human carcinoma-associated glycoprotein antigen recognized by mouse monoclonal antibody FU-MK-1. *Jpn J Cancer Res*, 91, 231-8.
20. Calabrese, G., Crescenzi, C., Morizio, E., Palka, G., Guerra, E. and Alberti, S. (2001) Assignment of TACSTD1 (alias TROP1, M4S1) to human chromosome 2p21 and refinement of mapping of TACSTD2 (alias TROP2, M1S1) to human chromosome 1p32 by in situ hybridization. *Cytogenet Cell Genet*, 92, 164-5.
21. Velders, M., Litvinov, S., Warnaar, S., Gorter, A., Fleuren, G., Zurawski, V., Jr. and Coney, L. (1994) New chimeric anti-pancarcinoma monoclonal antibody with superior Cytotoxicity-mediating potency. *Cancer Res*, 54, 1753-9.
22. Helfrich, W., ten Poele, R., Meersma, G., Mulder, N., de Vries, E., de Leij, L. and Smit, E. (1997) A quantitative reverse transcriptase polymerase chain reaction-based assay to detect carcinoma cells in peripheral blood. *Br J Cancer*, 76, 29-35.
23. Szala, S., Froehlich, M., Scollon, M., Kasai, Y., Steplewski, Z., Koprowski, H. and Linnenbach, A. (1990) Molecular cloning of cDNA for the carcinoma-associated antigen GA733-2. *Proc Natl Acad Sci USA*, 87, 3542-6.
24. Carter, C. L., C. Allen, and D. E. Henson, Relation of tumor size, lymph node status, and survival in 24,740 breast cancer cases. Cancer, 1989. 63(1): p. 181-7.
25. Goldhirsch, A., et al., *Meeting highlights: International Consensus Panel on the Treatment of Primary Breast Cancer. Seventh International Conference on Adjuvant Therapy of Primary Breast Cancer*. J Clin Oncol, 2001. 19(18): p. 3817-27.
26. Woo, C. S., et al., *Lymph node status combined with lymphovascular invasion creates a more powerful tool for predicting outcome in patients with invasive breast cancer*. Am J Surg, 2002. 184(4): p. 337-40.
27. Cummings, M. C., et al., *Occult axillary lymph node metastases in breast cancer do matter: results of 10-year survival analysis*. Am J Surg Pathol, 2002. 26(10): p. 1286-95.
28. de Mascarel, I., et al., *Prognostic significance of breast cancer axillary lymph node micrometastases assessed by two special techniques: reevaluation with longer follow-up*. Br J Cancer, 1992. 66(3): p. 523-7.
29. McGuckin, M. A., et al., *Occult axillary node metastases in breast cancer: their detection and prognostic significance*. Br J Cancer, 1996. 73(1): p. 88-95.
30. Sedmak, D. D., T. A. Meineke, and D. S. Knechtges, *Detection of metastatic breast carcinoma with monoclonal antibodies to cytokeratins*. Arch Pathol Lab Med, 1989. 113(7): p. 786-9.
31. Gardner, B. and J. Feldman, *Are positive axillary nodes in breast cancer markers for incurable disease?* Ann Surg, 1993. 218(3): p. 270-5; discussion 275-8.
32. Berns, E. M., et al., *c-myc amplification is a better prognostic factor than HER2/neu amplification in primary breast cancer*. Cancer Res, 1992. 52(5): p. 1107-13.
33. Datta, Y. H., et al., *Sensitive detection of occult breast cancer by the reverse-transcriptase polymerase chain reaction*. J Clin Oncol, 1994. 12(3): p. 475-82.
34. Gasparini, G., et al., *Prognostic significance of vascular endothelial growth factor protein in node-negative breast carcinoma*. J Natl Cancer Inst, 1997. 89(2): p. 139-47.
35. Ioachim; E., et al., *The prognostic significance of epidermal growth factor receptor (EGFR), C-erbB-2, Ki-67 and PCNA expression in breast cancer*. Anticancer Res, 1996. 16(5B): p. 3141-7.
36. Anan, K., et al., *Assessment of c-erbB2 and vascular endothelial growth factor mRNA expression in fine-needle aspirates from early breast carcinomas: pre-operative determination of malignant potential*. Eur J Surg Oncol, 1998. 24(1): p. 28-33.
37. Bieche, I., et al., *Prognostic value of chorionic gonadotropin beta gene transcripts in human breast carcinoma*. Clin Cancer Res, 1998. 4(3): p. 671-6.
38. Harbeck, N., et al., *Prognostic impact of tumor biological factors on survival in node-negative breast cancer*. Anticancer Res, 1998. 18(3C): p. 2187-97.
39. Linderholm, B., et al., *Vascular endothelial growth factor is of high prognostic value in node-negative breast carcinoma*. J Clin Oncol, 1998. 16(9): p. 3121-8.
40. Lockett, M. A., et al., *Detection of occult breast cancer micrometastases in axillary lymph nodes using a multimarker reverse transcriptase-polymerase chain reaction panel*. J Am Coll Surg, 1998. 187(1): p. 9-16.
41. Molina, R., et al., *c-erbB-2 oncoprotein, CEA, and CA 15.3 in patients with breast cancer: prognostic value*. Breast Cancer Res Treat, 1998. 51(2): p. 109-19.
42. Pathak, K. A., et al., *Carcinoembryonic antigen: an invaluable marker for advanced breast cancer*. J Postgrad Med, 1996. 42(3): p. 68-71.
43. Lockett, M. A., et al., *Efficacy of reverse transcriptase-polymerase chain reaction screening for micrometastic disease in axillary lymph nodes of breast cancer patients*. Am Surg, 1998. 64(6): p. 539-43; discussion 543-4.
44. Noguchi, S., et al., *Detection of breast cancer micrometastases in axillary lymph nodes by means of reverse transcriptase-polymerase chain reaction. Comparison between MUC1 mRNA and keratin 19 mRNA amplification*. Am J Pathol, 1996. 148(2): p. 649-56.
45. Mori, M., et al., *Detection of cancer micrometastases in lymph nodes by reverse transcriptase-polymerase chain reaction*. Cancer Res, 1995. 55(15): p. 3417-20.
46. Schoenfeld, A., et al., *Detection of breast cancer micrometastases in axillary lymph nodes by using polymerase chain reaction*. Cancer Res, 1994. 54(11): p. 2986-90.
47. Bostick, P. J., et al., *Limitations of specific reverse-transcriptase polymerase chain reaction markers in the detection of metastases in the lymph nodes and blood of breast cancer patients*. J Clin Oncol, 1998. 16(8): p. 2632-40.
48. Zippelius, A., et al., *Limitations of reverse-transcriptase polymerase chain reaction analyses for detection of* micrometastatic epithelial cancer cells in bone marrow [see comments]. J Clin Oncol, 1997. 15(7): p. 2701-8.
49. Eltahir, E. M., et al., *Putative markers for the detection of breast carcinoma cells in blood*. Br J Cancer, 1998. 77(8): p. 1203-7.
50. Giesing, M., et al., *Independent prognostication and therapy monitoring of breast cancer patients by DNA/RNA typing of minimal residual cancer cells*. Int J Biol Markers, 2000. 15(1): p. 94-9.
51. Goeminne, J. C., et al., *Unreliability of carcinoembryonic antigen (CEA) reverse transcriptase-polymerase chain reaction (RT-PCR) in detecting contaminating breast cancer cells in peripheral blood stem cells due to induction of CEA by growth factors*. Bone Marrow Transplant, 1999. 24(7): p. 769-75.
52. Gunn, J., et al., *Detection of micrometastases in colorectal cancer patients by K19 and K20 reverse-transcription polymerase chain reaction*. Lab Invest, 1996. 75(4): p. 611-6.
53. Lopez-Guerrero, J. A., et al., *Use of reverse-transcriptase polymerase chain reaction (RT-PCR) for carcinoembryonic antigen, cytokeratin 19, and maspin in the detection of tumor cells in leukapheresis products from patients with breast cancer: comparison with immunocytochemistry*. J Hematother, 1999. 8(1): p. 53-61.
54. Merrie, A. E., et al., *Analysis of potential markers for detection of submicroscopic lymph node metastases in breast cancer*. Br J Cancer, 1999. 80(12): p. 2019-24.
55. Zhong, X. Y., et al., *Evaluation of the reverse transcriptase/polymerase chain reaction for carcinoembryonic antigen for the detection of breast cancer dissemination in bone marrow and peripheral blood*. J Cancer Res Clin Oncol, 1999. 125(12): p. 669-74.
56. Zhong, X. Y., et al., *Analysis of sensitivity and specificity of cytokeratin 19 reverse transcriptase/polymerase chain reaction for detection of occult breast cancer in bone marrow and leukapheresis products*. J Cancer Res Clin Oncol, 1999. 125(5): p. 286-91.
57. Zach, O., et al., *Detection of circulating mammary carcinoma cells in the peripheral blood of breast cancer patients via a nested reverse transcriptase polymerase chain reaction assay for mammaglobin mRNA*. J Clin Oncol, 1999. 17(7): p. 2015-9.
58. Manzotti, M., et al., *Reverse transcription-polymerase chain reaction assay for multipe mRNA markers in the detection of breast cancer metastases in sentinel lymph nodes*. International Journal of Cancer, 2001. 95: p. 307-312.
59. Mitas, M., et al., *Prostate-Specific Ets (PSE) factor: a novel marker for detection of metastatic breast cancer in axillary lymph nodes*. Br J Cancer, 2002. 86(6): p. 899-904.
60. Henderson, A. R., *Assessing test accuracy and its clinical consequences: a primer for receiver operating characteristic curve analysis*. Ann Clin Biochem, 1993. 30 (Pt 6): p. 521-39.
61. Almeida, J. S., *Predictive non-linear modeling of complex data by artificial neural networks*. Curr Opin Biotechnol, 2002. 13(1): p. 72-6.
62. Goldhirsch, A., et al., *Meeting highlights: International Consensus Panel on the Treatment of Primary Breast Cancer*. J Natl Cancer Inst, 1998. 90(21): p. 1601-8.
63. Swets, J. A., *Measuring the accuracy of diagnostic systems*. Science, 1988. 240(4857): p. 1285-93.
64. Zehentner, B. K., et al., *Application of a multigene reverse transcription-PCR assay for detection of mammaglobin and complementary transcribed genes in breast cancer lymph nodes*. Clin Chem, 2002. 48(8): p. 1225-31.
65. Min, C. J., L. Tafra, and K. M. Verbanac, *Identification of superior markers for polymerase chain reaction detection of breast cancer metastases in sentinel lymph nodes*. Cancer Res, 1998. 58(20): p. 4581-4.
66. Marchetti, A., et al., *mRNA markers of breast cancer nodal metastases: comparison between mammaglobin and carcinoembryonic antigen in 248 patients*. J Pathol, 2001. 195(2): p. 186-90.
67. Masuda, N., et al., *Clinical significance of micrometastases in axillary lymph nodes assessed by reverse transcription-polymerase chain reaction in breast cancer patients*. Clin Cancer Res, 2000. 6(11): p. 4176-85.
68. Sakaguchi, M., et al., *Clinical relevance of reverse transcriptase-polymerase chain reaction for the detection of axillary lymph node metastases in breast cancer*. Ann Surg Oncol, 2003. 10(2): p. 117-25.
69. Watson, M. A., et al., *Mammaglobin expression in primary, metastatic, and occult breast cancer*. Cancer Res, 1999. 59(13): p. 3028-31.
70. Leygue, E., et al., *Mammaglobin, a potential marker of breast cancer nodal metastasis*. J Pathol, 1999. 189(1): p. 28-33.
71. Bostick, P. J., et al., *Detection of metastases in sentinel lymph nodes of breast cancer patients by multiple-marker RT-PCR*. Int J Cancer, 1998. 79(6): p. 645-51.
72. Smith, P. A., et al., *Submission of lymph node tissue for ancillary studies decreases the accuracy of conventional breast cancer axillary node staging*. Mod Pathol, 1999. 12(8): p. 781-5.
73. Metz, D. C. et al (1998) Yale J Biol Med 71, 81-90

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting metastasis of a non-small cell lung cancer or an esophageal cancer in a subject that has been previously diagnosed with non-small cell lung cancer or esophageal cancer, comprising detecting in a non-primary tissue of the subject overexpression of KS1/4 mRNA compared to a normal, control level of expression of KS1/4 mRNA in corresponding non-primary tissue, wherein the overexpression of KS1/4 mRNA in the subject's non-primary tissue indicates metastasis of a non-small cell lung cancer or an esophageal cancer in the subject.

2. The method of claim 1, wherein the cancer is non-small cell lung cancer.

3. The method of claim 1, wherein the non-primary tissue is a lymph node, bone marrow, bone, adipose tissue, or peripheral blood.

4. The method of claim 1, wherein the cancer is esophageal cancer.

5. The method of claim 3, wherein the non-primary tissue is a lymph node.

6. The method of claim 3, wherein the non-primary tissue is bone marrow.

7. The method of claim 3, wherein the non-primary tissue is bone.

8. The method of claim 3, wherein the non-primary tissue is adipose tissue.

9. The method of claim 3, wherein the non-primary tissue is peripheral blood.

* * * * *

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence

```
<220> FEATURE:
<223> OTHER INFORMATION: Description of Artificial Sequence; note =
      synthetic construct

<400> SEQUENCE: 1
cggatgaaac tctgagcaat gt                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
ctgcagttct gtgagccaaa g                                               21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
cgcagctcag gaagaatgtg                                                 20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
tgaagtacac tggcattgac ga                                              22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
gccaacaaag ctcaggacaa c                                               21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
gcagtgactt cgtcatttgg ac                                              22

<210> SEQ ID NO 7
<211> LENGTH: 19
<212> TYPE: DNA
<213> ORGANISM: Artificial Sequence
<220> FEATURE:
```

<223> OTHER INFORMATION: Description of Artificial Sequence; note =
       synthetic construct

<400> SEQUENCE: 7
ccctggaagc ctgcaaatt                                                19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence; note =
       synthetic construct

<400> SEQUENCE: 8
gaaccaactc aggcaggact tt                                            22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence; note =
       synthetic construct

<400> SEQUENCE: 9
accatcctat gagcgagtac c                                             21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence; note =
       synthetic construct

<400> SEQUENCE: 10
gccaccatta cctgcagaaa c                                             21

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence; note =
       synthetic construct

<400> SEQUENCE: 11
tgtagctgtt gcaaatgctt taagaaagaa gc                                 32

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence; note =
       synthetic construct

<400> SEQUENCE: 12
gggccactgt cgcatcatga ttgg                                          24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence; note = synthetic construct

<400> SEQUENCE: 13
catgaaagct gccttggaag a                                              21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 14
tgattctgcc gctcactatc ag                                             22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 15
gccgtgtgaa ccatgtgact tt                                             22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 16
ccaaatgcgg catcttcaaa                                                20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 17
agtgctcaag gacatcgaga cg                                             22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 18
agccacttct gcacattgct g                                              21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

```
<400> SEQUENCE: 19
agcagtgttt cctcaaccag tc                                              22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 20
tctgagccaa acgccttg                                                   18
```